US006794497B2

(12) United States Patent
Boldi et al.

(10) Patent No.: US 6,794,497 B2
(45) Date of Patent: Sep. 21, 2004

(54) AMINOFURANOSE COMPOUNDS

(75) Inventors: Armen M. Boldi, Burlingame, CA (US); Elaine B. Krueger, Pacifica, CA (US); Michael A. Walters, Novi, MI (US); Thutam P. Hopkins, Millbrae, CA (US); Meghan T. Keaney, Worcester, MA (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/054,019

(22) Filed: Jan. 22, 2002

(65) Prior Publication Data

US 2002/0173632 A1 Nov. 21, 2002

Related U.S. Application Data

(60) Provisional application No. 60/263,534, filed on Jan. 22, 2001.
(51) Int. Cl.$^7$ .............................. C07H 5/04; C07H 5/06; C07H 1/00
(52) U.S. Cl. ...................... 536/18.7; 536/1.11; 536/4.1; 536/17.2; 536/17.9; 536/18.1
(58) Field of Search .............................. 536/18.7, 1.11, 536/4.1, 17.2, 17.9, 18.1

(56) References Cited

U.S. PATENT DOCUMENTS 5,432,163 A * 7/1995 Akhtar et al.

FOREIGN PATENT DOCUMENTS

WO WO 96/35431 11/1990
WO WO 94/28910 12/1994

OTHER PUBLICATIONS

Marsault et al., "Oxazaphosphorinane Precursors to the Diastereoselective Synthesis of DNA Phosphorothioates", Tetrahedron, vol. 53, No. 50, pp. 16945–16958, 1997.*
Dhavale et al., "A New Route to Aminosugars From Sugar Nitrones: Synthesis of 6–Deoxynojirimycin", Tetrahedron Asymmetry, vol. 8, No. 9, pp. 1475–1486, 1997.*
Marsault et al., "Oxazaphosphorinane Precursors to the Diastereoselective Synthesis of DNA Phosphorothioates", Tetrahedron, vol. 53, No. 50, pp. 16945–16958, 1997.*
Tronchet et al., "Synthesis of Different Types of Amino Sugars Using Reductive Amination Reactions", Helvetica Chimica Acta, 1977, 60(6), pp. 1932–1934.*
Paulsen et al., Branched and Chain–extended Sugars, XXVIII; Synthesis of 6–amino–6–deoxyhepturonic Acids, Liebigs Annalen der Chemie, 1985, vol. 1, pp. 113–128.*
Reetz, et al, "A Highly Active Phosphine–free Catalyst System for Heck Reactions of Aryl Bromides", Tetrahedron Letters 39, 1998, pp 8449–8452.

Yu, et al, "Process Optimizzation in the Synthesis of 9–[2–(Diethylphosphonomethoxy)ethyl]adenine: Replacement of Sodium Hydride with Sodium tert–Butoxide as the Base for Oxygen Alkylation", Organic Process Research & Development, 1999, 3, pp 53–55.
Abdel–Magid, et al, "Reductive Amination of Aldehydes and Ketones by Using Sodium Triacetoxyborohydride", Tetrahedron Letters, 1990, vol. 31, No. 39, pp 5995–5998.
Abdel–Magid, et al, "Reductive Amination of Aldehydes and Ketones with Sodium Triacetoxyborohydride. Studies on Direct and Indirect Reductive Amination Procedures", J. Org. Chem, 1996, 61, pp 3849–3862.
Love, et al, "A Comparison of Imine Forming Methodologies", Organic Preparations and Procedures, Int., 31(4), 1999, pp 399–405.
Hicks, et al, Removal of Boric Acid and Related Compounds From Solutions of Carbohydrates With a Boron–Selective Resin (IRA–743), Carbohydrate Research, 147, (1986); pp 39–48.
Repic, Principles of Process Research and Chemical Development in the Pharmaceutical Industry, Wily; New York, NY; 1998; pp 71–74.
Kaldor, et al, "Use of Solid Supported Nucleophiles and Electrophiles for the Purification of Non–Peptide Small Molecule Libraries", Tetrahedron Letters, 1996, vol. 37, No. 40, pp 7193–7196.
Hodges, John C., "Covalent Scavengers for Primary and Secondary Amines", Synlett, 1999, No. 1, pp 152–158.
Gayo, et al, "Ion–Exchange Resins for Solutions Phase Parallel Synthesis of Chemical Libraries", Tetrahedron Letters, 1997, vol. 38, No. 4, pp 513–516.
Booth, et al, "Solid–Supported Reagent Strategies for Rapid Purification of Combinatorial Synthesis Products", Acc. Chem. Res., 1999, 32, pp 18–26.

(List continued on next page.)

Primary Examiner—James O. Wilson
Assistant Examiner—Traviss C. McIntosh, III
(74) Attorney, Agent, or Firm—Pfizer Inc.; Claude F. Purchase, Jr.

(57) ABSTRACT

The present invention provides compounds and methods of synthesizing furanose and aminofuranose compounds of Formula I

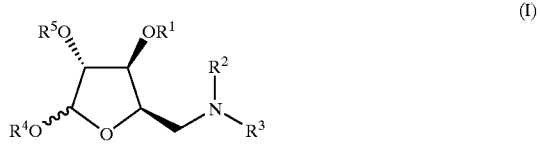

(I)

which are useful fro treating rheumatoid arthritis, immunomodulatory diseases and disorders, inflammation, and diseases and disorders characterized by exhibiting tissue proliferation.

1 Claim, No Drawings

OTHER PUBLICATIONS

Weidner, et al, "Polymer–assisted solution phase synthesis: a general method for sequestration of byproducts formed from activated acyl–transfer reactants", Tetrahedron Letters 40, 1999, pp 239–242.

Krueger, et al, "Solution–Phase Library Synthesis of Furanoses", Journal Combinatorial Chemistry, Apr. 9, 2002; pp A–J.

Kallus, et al, "Combinatorial Solid–Phase Synthesis Using D–Galactose as a Chiral Five–Dimension–Diversity Scaffold", Tetrahedron Letters 40, 1999; pp 7783–7786.

Tronchet, et al, "Analogues of Blocked Disaccharides bearing an N–Hydroxyimino and Nitroxyl Free Radicals thereof", J. Chem. Research (S), 1989, pp 334.

Moore, et al, "Dipolar Cycloaddition Reaction on a Soluble Polymer–Supported Dipolarophile: Synthesis of Sugar–derived Triazoles", Tetrahedron Letters 39 (1998), pp 7027–7030.

Hollingsworth, et al, "Toward a Carbohydrate–Based Chemistry: Progress in the Development of General–Purpose Chiral Synthons from Carbohydrates", Chem. Rev., 2000, pp A–P.

Hirschmann, et al, "Development of an Efficient, Regio– and Steroselective Route to Libraries Based on the –D–Glucose Scaffold", J. Org. Chem. 2000, 65, pp 8307–8316.

* cited by examiner

US 6,794,497 B2

AMINOFURANOSE COMPOUNDS

CROSS-REFERENCE TO RELATED APPLICATIONS

This application claims benefit of priority from U.S. provisional application No. 60/263,534, filed Jan. 22, 2001.

FIELD OF THE INVENTION

The present invention relates to the synthesis of furanose and aminofuranose compounds of Formula I.

BACKGROUND OF THE INVENTION

Synthesis of furanose and aminofuranose compounds of Formula I can be a time consuming task in spite of the different synthetic techniques known to one skilled in the art. The pharmaceutical industry thus always is in search of new processes that will enable synthesis of a large number of compounds at a relatively rapid pace. The present invention describes a process for rapid parallel synthesis of multiple furanose and aminofuranose compounds.

Related structures are known to exhibit biological activity. Amiprilose (Therafectin®), a related furanose compound, is being developed for the treatment of rheumatoid arthritis. 5,6-Dideoxy- and 5-amino- derivatives of idose and 6-deoxy, 6-amino derivatives of glucose exhibit immunomodulatory, anti-inflammatory, and anti-proliferative activity (Thomson, et al., WO 94/28910). Disubstituted and trisubstituted α-L-xylo-2-hexulofuranoses also exhibit anti-inflammatory and anti-proliferative properties (Arora, et al., WO 96/35431). It is expected that the compounds of Formula I exhibit similar properties.

SUMMARY OF THE INVENTION

The present invention pertains to furanose or aminofuranose compounds or an array of compounds of Formula I and their methods of synthesis. Also provided are novel compounds of Formula (7) and (7') which are useful intermediates the in synthesis of furanose and aminofuranose compounds, such as the compounds of Formula I.

DESCRIPTION OF THE INVENTION

Definitions

The following terms/phrases as used herein have the following meaning, unless indicated otherwise.

The term "array of compounds" or "library of compounds" indicates a collection of independent (individual) compounds that are synthesized by the process of the present invention. Generally the term array of compounds indicates a collection of individual compounds distinct from one another. Also included in the array (library) of compounds is a mixture of the individual compounds. The term "library of compounds" can be interchangeably used with the term "array of compounds".

The term "alkyl" is used to represent a straight (unbranched), branched or cyclic saturated hydrocarbon radical comprising from 1–14 carbon atoms, unless indicated otherwise and includes as methyl, ethyl, n-propyl, isopropyl, n-butyl, isobutyl, sec-butyl, tert-butyl and the like. The term "cycloalkyl" as used herein represents a stable 3- to 7- membered monocyclic or 7- to 10-membered polycyclic ring which is saturated or partially unsaturated (e.g., containing one or more double bonds). The foregoing alkyl group can be substituted with 1–3 substituents selected from the group consisting of $-C_{1-4}$alkyl, $=O$, $-N(C_{1-4}$alkyl$)_2$, $-OH$, $-O-C_{1-6}$alkyl, $-C(O)-O-C_{1-8}$alkyl, $-S-C_{1-4}$alkyl, cyano ($-C\equiv N$), $-CF_3$, aryl and heteroaryl. The foregoing cycloalkyl group can be substituted with 1–3 substituents selected from the group consisting of $-C_{1-4}$alkyl, $=O$, $-N(C_{1-4}$alkyl$)_2$, $-OH$, $-O-C_{1-6}$alkyl, $-C(O)-O-C_{1-8}$alkyl, $-S-C_{1-4}$alkyl, cyano ($-C\equiv N$), $-CF_3$, aryl and heteroaryl. Accordingly, the terms "alkyl" and "cycloalkyl" are intended to include both unsubstituted and substituted groups.

The term "aryl" is used to represent an aromatic monocyclic or polycyclic hydrocarbon radical comprising from 6–14 carbon atoms, unless indicated otherwise. Thus, an aryl group includes phenyl, naphthyl, anthracenyl, biphenyl, etc. The aryl group can be substituted with 1–3 substituents selected from the group consisting of alkoxy, $-C_{1-4}$alkyl, $-OCF_3$, $-CF_3$, halo, $-S$-alkyl, $-S$-haloalkyl, $-S$-haloaryl, $-NH(CH_2)_{1-4}-CN$, $-N[(CH_2)_{1-4}-CN]_2$, $-O-C_{1-6}$alkyl, $-C(O)-C_{1-4}$alkyl, $-O-C(O)-C_{1-4}$alkyl, $-N(C_{1-4}$alkyl$)_2$, $-NH-C(O)-C_{1-4}$alkyl and $-SO_2-NH_2$. Accordingly, the term "aryl" is intended to include both unsubstituted and substituted aryl groups.

The term "heterocycloalkyl" is intended to represent a stable 3- to 7- membered monocyclic or 7- to 10- membered polycyclic ring which is saturated or partially unsaturated (e.g., containing one or more double bonds) and contains carbon atoms and from 1 to 4 heteroatoms independently selected from N, O and S, while the term "heteroaryl" represents a stable 5- to 7- membered monocyclic or 7- to 10- membered polycyclic ring which is unsaturated and contains carbon atoms and from 1 to 4 heteroatoms independently selected from N, O, and S. The heteroatoms can be contained within a single ring (e.g., pyrazinyl, pyridyl, pyrazolyl, imidazolyl, pyrrolyl, thienyl, furyl, piperidyl, piperazinyl, morpholinyl, pyrrolidinyl, thiazolyl, pyrimidinyl, oxazolyl, isoxazolyl and the like) or within two rings (e.g., indolyl, quinolyl, benzofuranyl, purinyl and the like). The sulfur heteroatom can exist in its oxidation state, and the nitrogen can exist in its oxidation state or quaternized form. The heterocycloalkyl or heteroaryl ring may be attached to its pendent group at any heteroatom or carbon atom that results in a stable structure. The heterocycloalkyl ring may be substituted with 1–3 substituents selected from the group consisting of alkoxy, $-C_{1-4}$alkyl, $=O$, $-OCF_3$, $-CF_3$, halogen, $-S$-haloalkyl, $-S$-haloaryl, $-NH(CH_2)_{1-4}-CN$, $-N[(CH_2)_{1-4}-CN]_2$, $-O-C_{1-6}$alkyl, $-C(O)-C_{1-4}$alkyl, $-O-C(O)-C_{1-4}$alkyl, $-C(O)-O-C_{1-4}$alkyl, $-(CH_2)_{0-2}$-aryl, benzyl, $-SO_2-C_{1-4}$alkyl, $-SO_2$-aryl, $-SO_2$-heteroaryl, $-C(O)$-heteroaryl, heteroaryl, cycloalkyl, $-(CH_2)_{1-2}$-heterocycloalkyl, $-C(O)-N(C_{1-4}$alkyl$)_2$, $-C(O)-NH_2$ and $-NH-C(O)-C_{1-4}$alkyl. The heteroaryl ring may be substituted with 1-3 substituents selected from the group consisting of alkoxy, $-C_{1-4}$alkyl, $=O$, $-OCF_3$, $-CF_3$, halo, $-S$-haloalkyl, $-S$-haloaryl, $-NH(CH_2)_{1-4}-CN$, $-N[(CH_2)_{1-4}-CN]_2$, $-O-C_{1-6}$alkyl, $-C(O)-C_{1-4}$alkyl, $-O-C(O)-C_{1-4}$alkyl, $-C(O)-O-C_{1-4}$alkyl and $-NH-C(O)-C_{1-4}$alkyl. These substitutions can be on a carbon or a nitrogen atom if the resulting compound is stable. Accordingly, the terms "heterocycloalkyl" and "heteroaryl" are intended to include both unsubstituted and substituted groups.

The term "$(CH_2)_n$" refers to a straight carbon chain linker having "n" carbons (e.g., methylene, ethylene and so forth). When n is zero, the linker is a covalent bond.

The term "alkoxy" represents an oxygen atom attached to a $C_{1-4}$alkyl group, unless indicated otherwise.

The term "alkenyl" represents a straight chain or branched hydrocarbon group comprising 2–14 carbon atoms, unless indicated otherwise, and containing at least one carbon-carbon double bond. The alkenyl group can be substituted with a substituent selected from the group consisting of halo and aryl.

The term "alkynyl" refers to a straight (unbranched) or branched unsaturated hydrocarbon radical comprising from 2–8 carbon atoms, unless indicated otherwise, and containing about 1 to 3 triple bonds, such as ethynyl, 1-propynyl, 1-butynyl, 3-methylbut-1-ynyl, 1-pentynyl, and the like.

The term "halo" includes fluoro, chloro, bromo, and iodo.

The term "suitable amine substituent" as used herein represents any group ($R^8$), which is capable of forming a stable covalent bond with a nitrogen atom to form a compound of Formulas 30 and III. This phrase is intended to represent substituents that are known to and capable of forming a covalent bond with a nitrogen atom thereby forming a primary, secondary or tertiary amine. Illustrative examples of groups capable of forming a stable covalent bond with a nitrogen atom are H, alkyl, aryl, heteroaryl, alkyl-aryl, alkyl-heteroaryl, heterocyclyl, cycloalkyl or a combinations thereof. A comprehensive list of amines substituted with a substituted with suitable substituents can be found in the Aldrich Chemicals catalog, which is incorporated herein by reference.

The term "amino acid side chain" as used herein represents a natural or unnatural amino acid. The term "natural amino acid", as used herein is intended to represent the twenty naturally occurring amino acids in their 'L' form, which are some times also referred as 'common amino acids', a list of which can be found in *Biochemistry*, Harper & Row Publishers, Inc. (1983). The term "unnatural amino acid", as used herein, is intended to represent the 'D' form of the twenty naturally occurring amino acids described above. It is further understood that the term unnatural amino acid includes homologues of the natural amino acids, and synthetically modified form of the natural amino acids. The synthetically modified forms include amino acids having alkylene chains shortened or lengthened by up to two carbon atoms, amino acids comprising optionally substituted aryl groups, and amino acids comprised halogenated groups, preferably halogenated alkyl and aryl groups.

The term "natural amino acid side chain" is intended to represent a natural amino acid ("natural amino acid" as defined above) wherein a keto (C=O) group replaces the carboxylic acid group in the amino acid. Thus, for example, an alanine side chain is C(=O)—CH(NH$_2$)—CH$_3$; a valine side chain is C(=O)—CH(NH$_2$)—CH(CH$_3$)$_2$; and a cysteine side chain is C(=O)—CH(NH$_2$)—CH$_2$—SH. The term "unnatural amino acid side chain" is intended to represent an unnatural amino acid ("unnatural amino acid" as defined above) wherein a keto (C=O) group replaces the carboxylic acid group forming unnatural amino acid side chains similar to ones illustrated under the definition of "natural amino acid side chain" above.

As used in the present invention, the illustration:

generally indicates a point of attachment of the group, comprising the illustration, to another group or atom.

An "acid" as used herein represents a chemical entity capable of donating a proton (Brønsted acid) or accepting a pair of electrons (Lewis acid).

A "base" as used herein represents a chemical entity that can absorb or abstract a proton. Illustrative examples of bases include N-methylmorpholine, N-ethylmorpholine, N-methylpiperidine, N-ethylpiperidine, triethylamine, pyridine, lutidine, 1,8-diazabicyclo[5.4.0]undec-7-one, N,N-diisopropylethylamine, tetrabutylammonium hydroxide, tetramethylammonium hydroxide, lithium hydroxide, and aqueous solutions of alkali metal hydroxides, carbonates and bicarbonates, and so forth.

The term "solid support" or "SS", as used in the present invention, signifies polymeric material for supported synthesis. The solid support should be labile under certain conditions to facilitate formation of a compound of Formula I, and should otherwise be chemically stable under the conditions of the present method. Illustrative examples of suitable solid supports are Wang linker resins, 3,5-dimethoxy-4-formylphenoxy polystyrene; 2-(3,5-dimethoxy-4-formylphenoxy)ethoxymethyl polystyrene; 2-(3,5-dimethoxy-4-formylphenoxy)ethyl polystyrene; 4-(3,5-dimethoxy-4-formylphenoxy)-butyramidomethyl polystyrene; 4-(3,5-dimethoxy-4-formylphenoxy) propionamidomethyl polystyrene; and 4-(3,5-dimethoxy-4-formylphenoxy)acetamidomethyl. Other illustrative examples of solid supports can be found in The Combinatorial Index, B. A. Bunin, Academic Press (1998), which is incorporated herein by reference.

The term "suitable solvent" as used herein, is intended to indicate a medium/solvent that is compatible with the respective reaction conditions. Representative examples of suitable mediums/solvents include tetrahydrofuran, dioxane, toluene, N,N-dimethylformamide, dimethylsulfoxide, N,N-dimethyl acetamide, dichloromethane, N-methyl pyrrolidinone and mixtures thereof. A list of suitable mediums/solvents can be found in *Tetrahedron Letters* 39:8451–8454 (1998), which is incorporated herein by reference.

| Abbreviations | |
|---|---|
| AcOH | Acetic acid |
| AUC | Area Under the Curve |
| DCM | Dichloromethane |
| DIC | Diisopropylcarbodiimide |
| DMF | N,N-Dimethylformamide |
| DMSO | Dimethylsulfoxide |
| ESI | Electrospray ionization |
| EtOAc | Ethyl acetate |
| EtOH | Ethanol |
| Et$_2$O | Diethyl ether |
| FMOC | 9-fluorenylmethoxycarbonyl |
| HC(OMe)$_3$ | Trimethyl orthoformate |
| i-Pr$_2$NEt | N,N-diisopropylethylamine |
| KO t-Bu | Potassium tert-butoxide |
| NaBH(OAc)$_3$ | Sodium triacetoxyborohydride |
| NMM | N-Methylmorpholine |
| SS | Solid support |
| TFA | Trifluoroacetic acid |
| THF | Tetrahydrofuran |

One aspect of the invention provides convenient methods for synthesizing an individual compound or an array of compounds of Formula I:

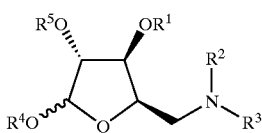
(I)

wherein:

R¹ is selected from the group consisting of —$C_{1-4}$alkyl and —$(CH_2)_{0-4}$-aryl;

R² is selected from the group consisting of —$C_{1-4}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl, —$(CH_2)_{0-2}$—O-aryl, —C(O)—$R^6$ and —C(O)—$NHR^6$, where $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

R³ is selected from the group consisting of —$C_{1-4}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$heteroaryl and —$(CH_2)_{0-2}$—O-aryl; or R² and R³ can be taken together to form a heterocycloalkyl;

R⁴ is selected from the group consisting of H, —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl; and R⁵ is H or can be taken together with R⁴ to form —$C(CH_3)_2$—.

One method of the invention is useful for synthesizing compounds of Formula Ia:

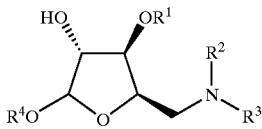
(Ia)

which are compounds of Formula I where R⁵ is H and R² is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl, and comprises the steps of:

(a) reacting a compound or an array of compounds of Formula 1:

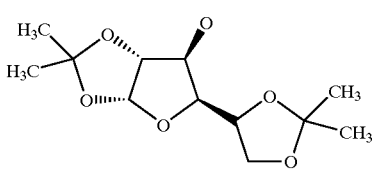
(1)

with an alkylating agent of Formula 2:

$R^1$—X (2)

in the presence of a deprotonation agent in a suitable solvent; where X is iodo or bromo and R¹ is as defined above, to yield an ether compound or an array of compounds of Formula 3:

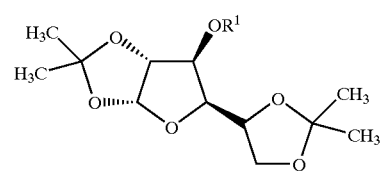
(3)

(b) reacting a compound or an array of compounds of Formula 3 with a hydrolysing agent, to form a diol compound or an array of compounds of Formula 4:

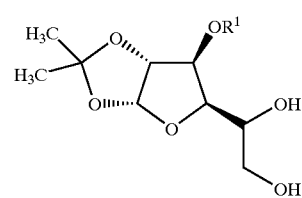
(4)

(c) reacting a compound or an array of compounds of Formula 4 with a cleaving agent in a suitable solvent to form an aldehyde compound or an array of compounds of Formula 5:

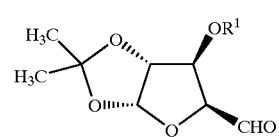
(5)

(d) reacting a compound or an array of compounds of Formula 5 with a secondary amine compound or an array of compounds of Formula 6:

$R^2R^3NH$ (6)

where R² and R³ are as defined above, and a reducing agent in a suitable solvent followed by treatment with a reducing agent scavenger resin in a suitable solvent and an amine scavenger resin in a suitable solvent to form a tertiary amine compound or an array of compounds of Formula 7:

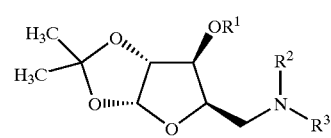
(7)

(e) reacting a compound or an array of compounds of Formula 7 with a compound or an array of compounds of Formula 8:

$R^4OH$ (8)

where R⁴ is selected from the group consisting of —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl, and an acid in a suitable solvent followed by treatment with an acid scavenger resin in a suitable solvent to form a compound or an array of compounds of Formula Ia.

The solvents used in steps (a)–(e) can be independently selected from the group consisting of DCM, THF, 1,4-dioxane, EtOH (and other lower alkyl alcohols such as methanol), and mixtures thereof. For step (d ), 1,4-dioxane is particularly preferred.

In step (a), the deprotonation agent can be KOH (e.g., in DMSO solvent) or KO t-Bu (e.g., in THF solvent), and is preferably KO t-Bu. An alternate embodiment of the invention uses dimethyl sulfate as the alkylating agent in step (a) rather than the compound of Formula 2. In step (b), the hydrolysing agent is preferably 70% AcOH in water. In step (c), the cleaving agent is preferably NaIO$_4$ adsorbed on silica gel. In step (d), the reducing agent can be NaBH(OAc)$_3$, NaBH$_4$, BH$_3$ in pyridine and H$_2$/Pd catalyst, and is preferably NaBH(OAc)$_3$. The reducing agent scavenger resin for borate is preferably Amberlite IRA-743 resin and the amine scavenger resin is preferably SS-isocyanate resin or SS-4-benzyloxybenzaldehyde resin. In step (d), preferably an excess ($\geq 1$ equivalents) of the secondary amine compound of Formula 6 is used. Also in step (d), preferably an excess of the reducing agent is used. In step (e), the acid is can be HCl, triflic acid, HBr, TFA, H$_2$SO$_4$ and p-toluenesulfonic acid, and is preferably 4M HCl in 1,4-dioxane and the acid scavenger resin is preferably SS-methylpiperidine resin.

Another method of the invention is useful for synthesizing compounds of Formula Ib:

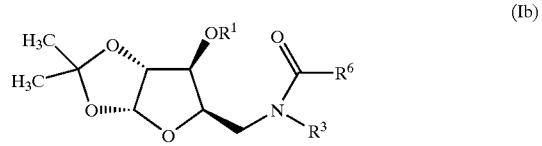

(Ib)

which are compounds of Formula I where R$^5$ is taken together with R$^4$ to form —C(CH$_3$)$_2$— and R$^2$ is —C(O)—R$^6$, where R$^6$ is as defined above, and comprises the steps of:

(a), (b) and (c) as described above, to form an aldehyde compound or an array of compounds of Formula 5:

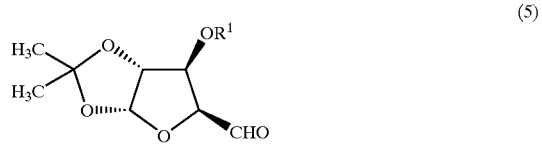

(5)

(d') reacting a compound or an array of compounds of Formula 5 with a primary amine compound or an array of compounds of Formula 6':

(6')

where R$^3$ is as defined above, and a reducing agent in a suitable solvent followed by treatment with a reducing agent scavenger resin in a suitable solvent and an amine scavenger resin in a suitable solvent to form a secondary amine compound or an array of compounds of Formula 7':

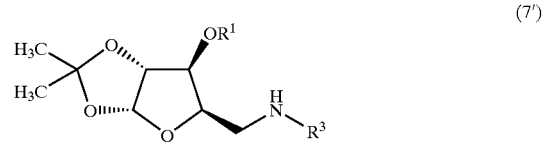

(7')

(e') reacting a compound or an array of compounds of Formula 7' with an acid chloride compound or an array of compounds of Formula 9:

(9)

where R$^6$ is as defined above, and a suitable base in a suitable solvent followed by treatment with an acid chloride scavenger resin in a suitable solvent to form a compound or an array of compounds of Formula Ib.

The solvents used in steps (d')–(e')can be independently selected from the group consisting of DCM, THF, 1,4-dioxane, EtOH (and other lower alkyl alcohols such as methanol), and mixtures thereof. For step (d'), 1,4-dioxane is particularly preferred. In step (d'), the reducing agent is NaBH(OAc)$_3$, NaBH$_4$BH$_3$ in pyridine and H$_2$/Pd catalyst, and is preferably NaH(OAc)$_3$. The reducing agent scavenger resin for borate is preferably Amberlite IRA-743 resin and the amine scavenger resin is preferably SS-isocyanate resin. In step (d'), preferably an excess of the primary amine compound of Formula 6' is used, and more preferably 3 equivalents. Also in step (d'), an excess of the reducing agent is used. In step (e'), the base can be NMM, triethylamine, N,N-diisopropylethylamine, pyridine and 2,6-lutidine, and is preferably NMM. The acid chloride scavenger resin is preferably Dowex SBr LC NG OH anion exchange resin.

Another method of the invention is useful for synthesizing compounds of Formula Ic:

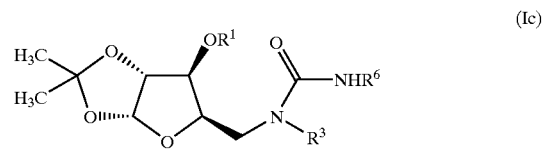

(Ic)

which are compounds of Formula I where R$^5$ is taken together with R$^4$ to form —C(CH$_3$)$_2$— and R$^2$ is —C(O)—NHR$^6$, where R$^6$ is as defined above, and comprises the steps of:

(a), (b) and (c) as described above, to form an aldehyde compound or an array of compounds of Formula 5:

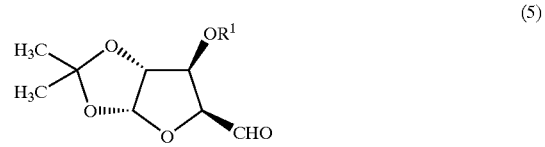

(5)

(d') reacting a compound or an array of compounds of Formula 5 with a primary amine compound or an array of compounds of Formula 6':

(6')

where R$^3$ is as defined above, and a reducing agent in a suitable solvent followed by treatment with a reducing agent scavenger resin in a suitable solvent and an amine scavenger resin in a suitable solvent to form a secondary amine compound or an array of compounds of Formula 7':

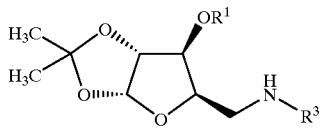

(7')

(e'') reacting a compound or an array of compounds of Formula 7' with an isocyanate compound or an array of compounds of Formula 10:

$$R^6NCO \quad (10)$$

where $R^6$ is as defined above, in a suitable solvent followed by treatment with an isocyanate scavenger resin in a suitable solvent to form a compound or an array of compounds of Formula Ic.

The solvents used in steps (e'') can be independently selected from the group consisting of DCM, THF, 1,4-dioxane, EtOH and mixtures thereof. The preferred reagents for step (d') are as described above. In step (e'), the isocyanate scavenger resin can be SS-tris(2-aminoethyl)amine resin or SS-aminomethyl resin, and is preferably SS-tris(2-aminoethyl)amine resin.

Another method of the invention is useful for the hydrolysis of compounds of Formula 7', Ib and Ic into hemi acetals. These hemi acetals are referred to as compounds of Formulas IIa, IIb and IIc:

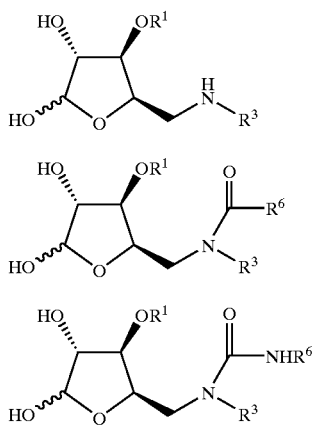

wherein:
  $R^1$ is selected from the group consisting of —$C_{1-4}$alkyl and —$(CH_2)_{0-4}$-aryl;
  $R^3$ is selected from the group consisting of —$C_{1-4}$alkyl, —$(CH_2)_{0-2}$-cycloalkyl, —$C_2$ alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; and
  $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl.

This method for the hydrolysis of compounds of Formulas 7', Ib and Ic comprises the step of reacting these compounds with an acid and water in a suitable solvent, to yield compounds of Formula IIa, IIb and IIc respectively. A suitable acid is HCl and a suitable solvent is 1,4-dioxane.

Another aspect of the invention pertains to solid-phase syntheses of a related group of compounds of Formula III:

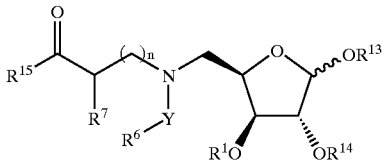

(III)

wherein:
  $R^1$ is selected from the group consisting of —$C_{1-4}$alkyl and —$(CH_2)_{0-4}$-aryl;
  Z is selected from the group consisting of —C(O)— and —C(O)—NH—;
  $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;
  $R^7$ is an amino acid side chain;
  $R^{13}$ and $R^{14}$ are H or are taken together to form —$C(CH_3)_2$—;
  $R^{15}$ is selected from the group consisting of —OH and —$NHR^8$, where $R^8$ is any suitable amine substituent; and
  n is an integer from 1–14.

The details of these solid phase methods are set forth in the Experimental Details section.

In a preferred embodiment, the methods of the invention are used to synthesize a compound or an array of compounds of Formula I having the following preferred substituents.

$R^1$ is preferably selected from the group consisting of —$C_{1-6}$alkyl and —$CH_2$-aryl. Preferred —$C_{1-6}$alkyl groups are methyl, ethyl, butyl and propyl. Preferred —$CH_2$-aryl groups are benzyl, 3-methoxybenzyl and —$CH_2$-naphthyl.

$R^2$ is preferably selected from the group consisting of —$C_{1-6}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl, —$(CH_2)_{0-2}$—O-aryl, —C(O)—$R^6$ and —C(O)—$NHR^6$:

$R^3$ is preferably selected from the group consisting of —$C_{1-6}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl, or is taken together to form a heterocycloalkyl.

For the $R^2$ and $R^3$ substituents, preferred —$C_{1-6}$alkyl groups are methyl, ethyl, propyl, 2-propyl, butyl, isobutyl, hexyl, —$CH(CH_2CH_3)_2$, —$CH_2CF_3$, —$CH_2$—C≡N, —$(CH_2)_2$—C≡N, —$(CH_2)_2$—$N(CH_3)_2$, —$(CH_2)_3$—$N(CH_3)_2$, —$(CH_2)_2$—$N(CH_2CH_3)_2$, —$(CH_2)_2$—O—$CH_3$, —$(CH_2)_2$—O—$CH_2CH_3$, —$(CH_2)_3$—O—$CH_3$, —CH$(CH_3)$—$CH_2$—O—$CH_3$, —$CH_2$—$C(CH_3)_2$—$C_6H_5$, —$CH_2$—$CH(C_6H_5)_2$,

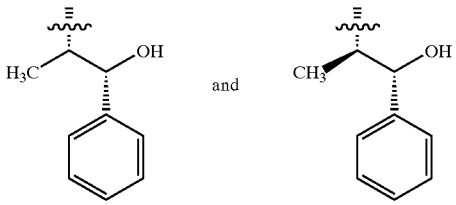

For the $R^2$ and $R^3$ substituents, preferred —$(CH_2)_{0-2}$-cycloalkyl groups are cyclohexyl, —$(CH_2)$-cyclopropyl,

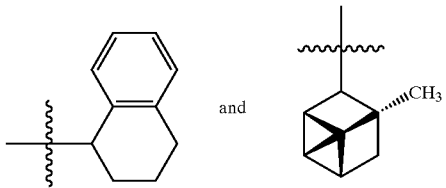

For the $R^2$ and $R^3$ substituents, a preferred —$C_2$akenyl group is —$CH_2$—$CH=CH_2$.

For the $R^2$ and $R^3$ substituents, preferred —$(CH_2)_{1-4}$-aryl groups are —$CH_2$-naphthyl and —$(CH_2)_{1-3}$—$C_6H_5$, where phenyl can be substituted with 1–3 groups selected from the group consisting of —$CH_3$, —$OCH_3$, —$OCH_2CH_3$, —$OCF_3$, —$CF_3$, —F, —Br and —Cl.

For the $R^2$ and $R^3$ substituents, preferred —$(CH_2)_{0-4}$-heterocycloalkyl groups are selected from the group consisting of

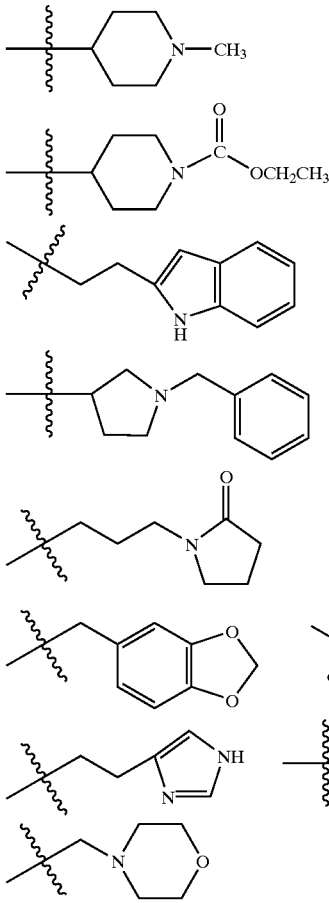

For the $R^2$ and $R^3$ substituents, preferred —$(CH_2)_{1-4}$-heteroaryl groups are selected from the group consisting of

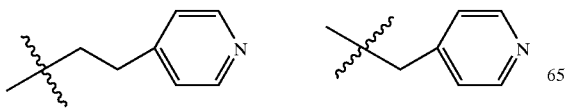

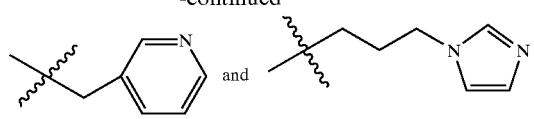

For the $R^2$ and $R^3$ substituents, a preferred —$(CH_2)_{0-2}$—O-aryl group is —$(CH_2)_2$—O—$C_6H_5$.

When the $R^2$ substituent is a —C(O)—$R^6$ group or a —C(O)—$NHR^6$ group, the preferred $R^6$ —$C_{1-4}$alkyl group is selected from the group consisting of ethyl, 2-propyl, —$CH_2$—O—$CH_3$ and —$CH(C_6H_5)_2$. The preferred $R^6$—$(CH_2)_{0-2}$—O-aryl group is —$CH_2$—O—$C_6H_5$. The preferred $R^6$ —$C_{2-6}$alkenyl group is selected from the group consisting of —$CH_2$—$CH=CH_2$ and

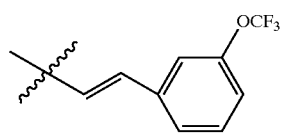

The preferred $R^6$—$(CH_2)_{0-2}$-cycloalkyl group is cyclohexyl. The preferred $R^6$—$(CH_2)_{1-4}$-aryl group is selected from the group consisting of —$(CH_2)_{0-2}$—$C_6H_5$ (where phenyl can be substituted with 1–3 groups selected from the group consisting of methyl, 2-propyl, —$OCH_3$, —$OCH_2CH_3$, —$O(CH_2)_3CH_3$, —$OCF_3$, —$CF_3$, —$C\equiv N$, —$C(O)CH_3$, —$SCH_3$, —F and —Cl), When the $R^2$ and $R^3$ substituents are taken together to form a heterocycloalkyl, the

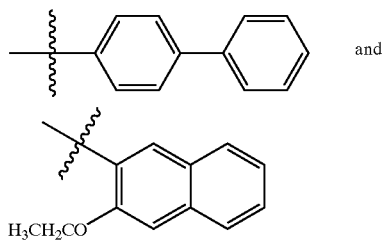

preferred heterocycloalkyl groups include:

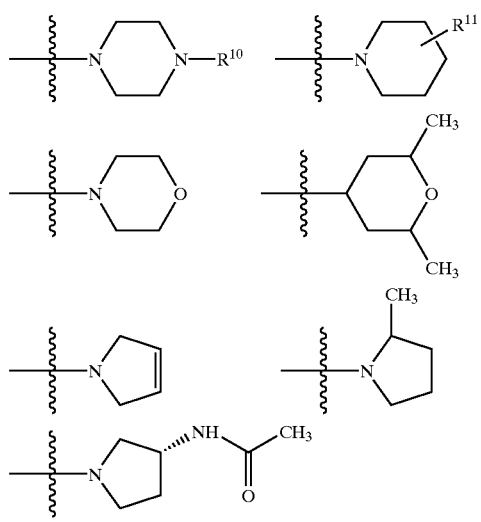

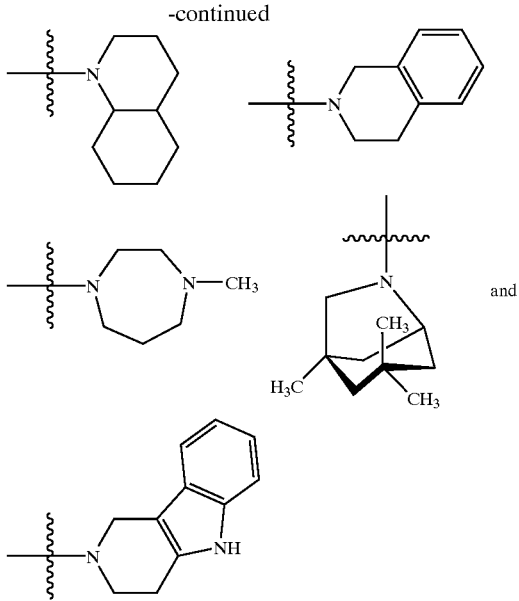

where $R^{10}$ is selected from the group consisting of —$C_{1-4}$alkyl, —$(CH_2)_{0-2}$-aryl, —$C(O)$-$C_{1-4}$alkyl, —$C(O)$—$O$—$C_{1-4}$alkyl, —$SO_2$—$C_{1-4}$alkyl, —$SO_2$-aryl, —$SO_2$-heteroaryl, —$C(O)$-heteroaryl, heteroaryl, cycloalkyl and —$(CH_2)_{1-2}$-heterocycloalkyl; and where $R^{11}$ is selected from the group consisting of —$C_{1-4}$alkyl, —$(CH_2)_{0-2}$-aryl, —$C(O)$—$O$—$C_{1-4}$alkyl, —$C(O)$—$N(C_{1-4}$alkyl$)_2$, —$C(O)$—$NH_2$, —$C(OH)(C_6H_5)_2$ and

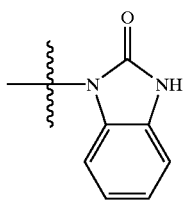

For the $R^{10}$ substituent, preferred —$C_{1-4}$alkyl groups are methyl, ethyl and —$CH_2CH_2OH$.

For the $R^{10}$ substituent, preferred —$(CH_2)_{0-2}$-aryl groups are —$CH_2$—$C_6H_5$ and —$C_6H_5$, where phenyl can be substituted with 1–2 groups selected from the group consisting of —$CH_3$, —$OCH_3$, —$C(O)CH_3$, —$OCF_3$ and —F.

For the $R^{10}$ substituent, a preferred —$C(O)$—$C_{1-4}$alkyl group is —$C(O)CH_3$.

For the $R^{10}$ substituent, a preferred —$C(O)$—$O$—$C_{1-4}$alkyl group is —$C(O)$—$OCH_2CH_3$.

For the $R^{10}$ substituent, a preferred —$SO_2$—$C_{1-4}$alkyl group is —$SO_2$—$CH_3$.

For the $R^{10}$ substituent, a preferred —$SO_2$-aryl group is —$SO_2$—$C_6H_5$.

For the $R^{10}$ substituent, a preferred —$SO_2$-heteroaryl group is

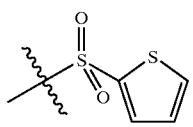

For the $R^{10}$ substituent, preferred —$C(O)$-heteroaryl groups are

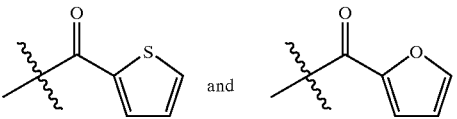

For the $R^{10}$ substituent, preferred heteroaryl groups are

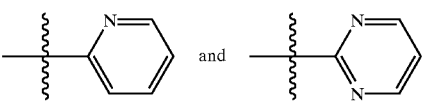

For the $R^{10}$ substituent, a preferred cycloalkyl group is cyclohexyl.

For the $R^{10}$ substituent, a preferred —$(CH_2)_{1-2}$-heterocycloalkyl group is

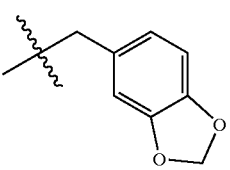

For the $R^{11}$ substituent, preferred —$C_{1-4}$alkyl groups are methyl, ethyl and —$CH_2CH_2OH$.

For the $R^{11}$ substituent, a preferred —$(CH_2)_{0-2}$-aryl group is —$CH_2$—$C_6H_5$.

For the $R^{11}$ substituent, a preferred —$C(O)$—$O$—$C_{1-4}$ alkyl group is —$C(O)$—$O$—$CH_2CH_3$.

For the $R^{11}$ substituent, a preferred —$C(O)$—$N(C_{1-4}$ alkyl$)_2$ group is —$C(O)$—$N(CH_2CH_3)_2$.

$R^4$ is preferably selected from the group consisting of —$C_{1-6}$alkyl, —$(CH_2)_{0-2}$-cycloalkyl, —$C_{2-6}$alkenyl, —$C_{2-8}$ alkynyl and —$(CH_2)_{1-2}$-heterocycloalkyl. Preferred —$C_{1-6}$ alkyl groups are methyl, ethyl, propyl, butyl, isobutyl, isoamyl, —$CH_2$—$S$—$CH_2CH_3$, —$(CH_2)_2$—$S$—$CH_3$, —$CH_2$—$O$—$CH_2$—$CH(CH_3)_2$, —$(CH_2)_2$—$O$—$CH_3$, —$(CH_2)_2$—$O$—$CH(CH_3)_2$, —$(CH_2)_3$—$O$—$CH_2CH_3$, —$CH(CH_3)$—$CH_2$—$O$—$CH_2CH_3$ and —$(CH_2)_2$—$CH(CH_3)_2$—$O$—$CH_3$. Preferred —$(CH_2)_{0-2}$-cycloalkyl groups are —$(CH_2)$-cyclopropyl, cyclohexyl and

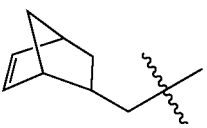

Preferred —$C_{2-6}$alkenyl groups are —$CH_2$—$CH$=$C(CH_3)$ $CH_3$, —$CH_2$—$CH$=$CH_2$, —$CH_2$—$CH$=$CH$—$CH_2Cl$ and —$CH_2$—$CH$=$CH$—$CH_3$. A preferred —$C_{2-8}$alkynyl group is —$CH_2$—$C$≡$C$—$CH_2CH_3$. A preferred —$(CH_2)_{1-2}$-heterocycloalkyl group is

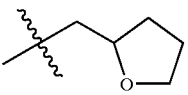

Another aspect of the present invention pertains to novel compounds or a library of compounds of Formula I, 7 and 7' and their method of synthesis, as described above.

Preferred compounds of Formulas 7 and 7' have $R^1$ and $R^3$ substituents as described above for the preferred compounds of Formula I.

Other invention embodiments are described below:

1. A method for the synthesis of a compound of Formula Ia:

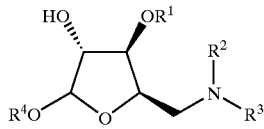
(Ia)

wherein:

$R^1$ is selected from the group consisting of —$C_{1-14}$alkyl and —$(CH_2)_{0-4}$-aryl;

$R^2$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl;

$R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^2$ and $R^3$ can be taken together with the nitrogen atom to which they are attached to form a heterocycloalkyl; and $R^4$ is selected from the group consisting of H, —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl;

which comprises the steps of:

(a) reacting a compound of Formula 1:

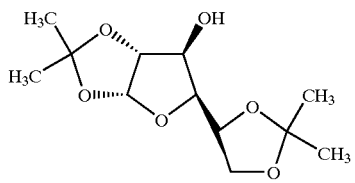
(1)

with an alkylating agent of Formula (2):

$R^1$—X (2)

in the presence of a deprotonation agent in a suitable solvent; where X is iodo or bromo and $R^1$ is as defined above, to yield an ether compound of Formula (3):

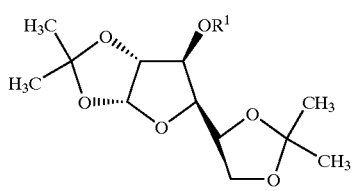
(3)

(b) reacting a compound of Formula (3) with a hydrolysing agent to form a diol compound of Formula (4):

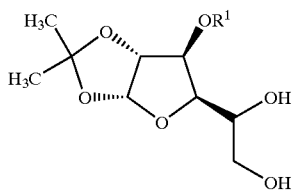
(4)

(c) reacting a compound of Formula (4) with a cleaving agent in a suitable solvent to form an aldehyde compound of Formula (5):

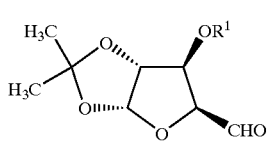
(5)

(d) reacting a compound of Formula (5) with a secondary amine compound of Formula (6):

$R^2R^3NH$ (6)

where $R^2$ and $R^3$ are as defined above, and a reducing agent in a suitable solvent followed by treatment with a reducing agent scavenger resin in a suitable solvent and an amine scavenger resin in a suitable solvent to form a tertiary amine compound of Formula (7):

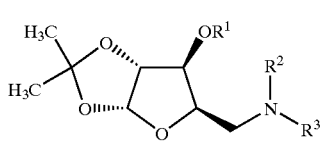
(7)

(e) reacting a compound of Formula (7) with a compound of Formula (8):

$R^4OH$ (8)

where $R^4$ is selected from the group consisting of H, —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl, and an acid in a suitable solvent followed by treatment with an acid scavenger resin in a suitable solvent to form a compound of Formula Ia.

2. The method of Embodiment 1 wherein the suitable solvents are independently selected from the group consisting of dichloromethane, tetrahydrofuran, 1,4-dioxane, lower alkyl alcohols, and mixtures thereof.

3. The method of Embodiment 1 wherein the deprotonation agent in step (a) is KOH or potassium tert-butoxide.

4. The method of Embodiment 1 wherein the hydrolysing agent in step (b) is 70% acetic acid in water.

5. The method of Embodiment 1 wherein the cleaving agent in step (c) is $NaIO_4$ adsorbed on silica gel.

6. The method of Embodiment 1 wherein the reducing agent in step (d) is selected from the group consisting of $NaBH(OAc)_3$, $NaBH_4$, $BH_3$ in pyridine, and $H_2$/Pd catalyst.

7. The method of Embodiment 1 wherein the amine scavenger resin in step (d) is solid support-bound isocyanate or benzyloxybenzaldehyde resin.

8. The method of Embodiment 1 wherein in step (d) an excess of the secondary amine compound of Formula (6) is used.
9. The method of Embodiment 1 wherein in step (d), an excess of the reducing agent is used.
10. The method of Embodiment 1 wherein the acid in step (e) is selected from the group consisting of HCl, triflic acid, HBr, trifluoroacetic acid, $H_2SO_4$ and p-toluenesulfonic acid.
11. The method of Embodiment 1 wherein the acid scavenger resin in step (e) is solid support-bound methylpiperidine resin.
12. A method for the synthesis of a compound of Formula Ib:

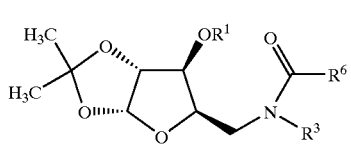
(Ib)

wherein:
$R^1$ is selected from the group consisting of —$C_{1-14}$alkyl and —$(CH_2)_{0-4}$-aryl;
$R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^6$ and $R^3$ can be taken together with the carbon and nitrogen atoms, respectively, to which they are attached to form a heterocycloalkyl containing an oxo (=O) substitution at the carbon atom; and
$R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;
which comprises the steps of:
(a) reacting a compound of Formula (1):

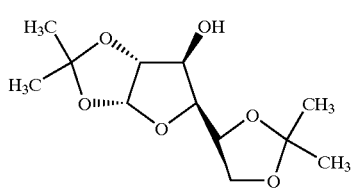
(1)

with an alkylating agent of Formula (2):

$$R^1—X \quad (2)$$

in the presence of a deprotonation agent in a suitable solvent; where X is iodo or bromo and $R^1$ is as defined above, to yield an ether compound of Formula (3):

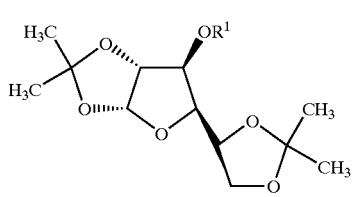
(3)

(b) reacting a compound of Formula (3) with a hydrolysing agent, to form a diol compound of Formula (4):

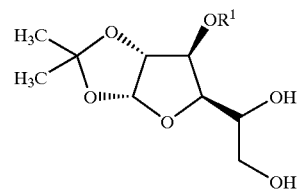
(4)

(c) reacting a compound of Formula (4) with a cleaving agent in a suitable solvent to form an aldehyde compound of Formula (5):

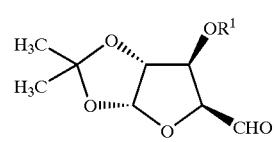
(5)

(d') reacting a compound of Formula (5) with a primary amine compound of Formula (6'):

$$R^3NH_2 \quad (6')$$

where $R^3$ is as defined above, and a reducing agent in a suitable solvent followed by treatment with a reducing agent scavenger resin in a suitable solvent and an amine scavenger resin in a suitable solvent to form a secondary amine compound of Formula (7'):

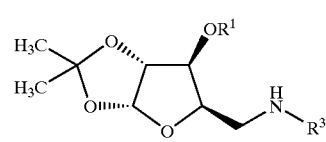
(7')

(e') reacting a compound of Formula (7') with an acid chloride compound of Formula (9):

$$R^6COCl \quad (9)$$

where $R^6$ is as defined above, and a suitable base in a suitable solvent followed by treatment with an acid chloride scavenger resin in a suitable solvent to form a compound of Formula Ib.
13. The method of Embodiment 12 wherein the suitable solvents are independently selected from the group consisting of dichloromethane, tetrahydrofuran, 1,4-dioxane, lower alkyl alcohols, and mixtures thereof.
14. The method of Embodiment 12 wherein the deprotonation agent in step (a) is KOH or potassium tert-butoxide.
15. The method of Embodiment 12 wherein the hydrolysing agent in step (b) is 70% acetic acid in water.
16. The method of Embodiment 12 wherein the cleaving agent in step (c) is $NaIO_4$ adsorbed on silica gel.
17. The method of Embodiment 12 wherein the reducing agent in step (d') is selected from the group consisting of $NaBH(OAc)_3$, $NaBH_4$, $BH_3$ in pyridine and $H_2$/Pd catalyst.
18. The method of Embodiment 12 wherein the amine scavenger resin in step (d') is solid support-bound isocyanate.
19. The method of Embodiment 12 wherein in step (d'), an excess of the primary amine compound of Formula (6') is used.

20. The method of Embodiment 12 wherein in step (d') an excess of the reducing agent is used.

21. The method of Embodiment 12 wherein the base in step (e') is selected from the group consisting of N-methylmorpholine, triethylamine, N,N-diisopropylethylamine, pyridine and 2,6-lutidine.

22. A method for the synthesis of a compound of Formula Ic:

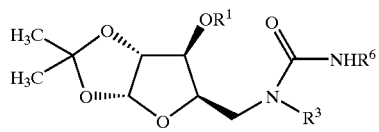
(Ic)

wherein:

R$^1$ is selected from the group consisting of —C$_{1-14}$alkyl and —(CH$_2$)$_{0-4}$-aryl;

R$^3$ is selected from the group consisting of —C$_{1-14}$alkyl, —(CH$_2$)$_{0-2}$-cycloalkyl, —C$_{2-6}$alkenyl, —(CH$_2$)$_{1-4}$-aryl, —(CH$_2$)$_{0-4}$-heterocycloalkyl, —(CH$_2$)$_{1-4}$-heteroaryl and —(CH$_2$)$_{0-2}$—O-aryl; or R$^6$ and R$^3$ can be taken together with the carbon and nitrogen atoms, respectively, to which they are attached to form a heterocycloalkyl containing an oxo (=O) substitution at the carbon atom; and R$^6$ is selected from the group consisting of —C$_{1-4}$alkyl, —(CH$_2$)$_{0-2}$—O-aryl, —C$_{2-6}$alkenyl, —(CH$_2$)$_{0-2}$-cycloalkyl and —(CH$_2$)$_{1-4}$-aryl;

which comprises the steps of:

(a) reacting a compound of Formula 1:

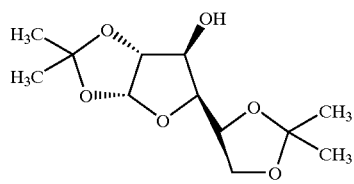
(1)

with an alkyating agent of Formula (2):

R$^1$—X (2)

in the presence of a deprotonation agent in a suitable solvent; where X is iodo or bromo and R$^1$ is as defined above, to yield an ether compound of Formula (3):

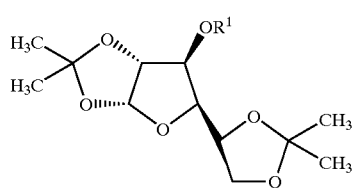
(3)

(b) reacting a compound of Formula (3) with a hydrolysing agent, to form a diol compound of Formula (4):

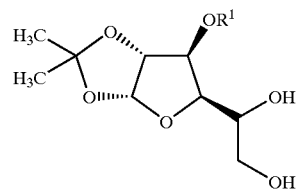
(4)

(c) reacting a compound of Formula (4) with a cleaving agent in a suitable solvent to form an aldehyde compound of Formula (5):

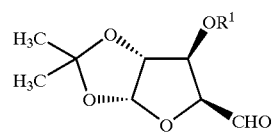
(5)

(d') reacting a compound of Formula (5) with a primary amine compound of Formula (6'):

R$^3$NH$_2$ (6')

where R$^3$ is as defined above, and a reducing agent in a suitable solvent followed by treatment with a reducing agent scavenger resin in a suitable solvent and an amine scavenger resin in a suitable solvent to form a secondary amine compound of Formula (7'):

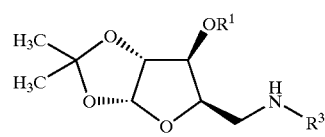
(7')

(e'') reacting a compound of Formula (7') with an isocyanate compound of Formula (10):

R$^6$NCO (10)

where R$^6$ is as defined above, in a suitable solvent followed by treatment with an isocyanate scavenger resin in a suitable solvent to form a compound of Formula Ic.

23. The method of Embodiment 22 wherein the suitable solvents are independently selected from the group consisting of dichloromethane, tetrahydrofuran, 1,4-dioxane, lower alkyl alcohols, and mixtures thereof.

24. The method of Embodiment 22 wherein the deprotonation agent in step (a) is KOH or potassium tert-butoxide.

25. The method of Embodiment 22 wherein the hydrolysing agent in step (b) is 70% acetic acid in water.

26. The method of Embodiment 22 wherein the cleaving agent in step (c) is NaIO$_4$ adsorbed on silica gel.

27. The method of Embodiment 22 wherein the reducing agent in step (d') is selected from the group consisting of NaBH(OAc)$_3$, NaBH$_4$, BH$_3$ in pyridine, and H$_2$/Pd catalyst.

28. The method of Embodiment 22 wherein the amine scavenger resin in step (d') is solid support-bound isocyanate.

29. The method of Embodiment 22 wherein in step (d') an excess of the primary amine compound of Formula (6') is used.

30. The method of Embodiment 22 wherein in step (d') an excess of the reducing agent is used.
31. The method of Embodiment 22 wherein the isocyanate scavenger resin in step (e") is solid support-bound tris(2-aminoethyl)amine or aminomethyl resin.
32. A method for the synthesis of a compound of Formula (7):

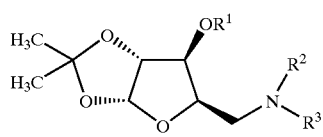

(7)

wherein:

$R^1$ is selected from the group consisting of —$C_{1-14}$alkyl and —$(CH_2)_{0-4}$-aryl;

$R^2$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl, —$(CH_2)_{0-2}$—O-aryl, —C(O)—$R^{16}$ and —C(O)—$NHR^6$, where $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl; and $R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^2$ and $R^3$ can be taken together with the nitrogen atom to which they are attached to form a heterocycloalkyl;

which comprises the steps of:

(a) reacting a compound of Formula 1:

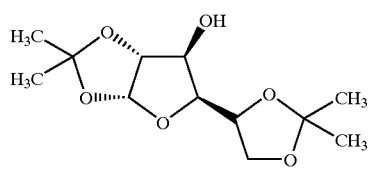

(1)

with an alkylating agent of Formula (2):

$R^1$—X (2)

in the presence of a deprotonation agent in a suitable solvent; where X is iodo or bromo and $R^1$ is as defined above, to yield an ether compound of Formula (3):

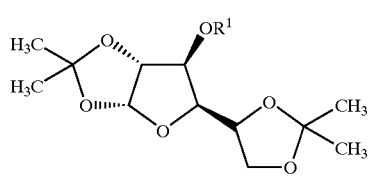

(3)

(b) reacting a compound of Formula (3) with a hydrolysing agent, to form a diol compound of Formula (4):

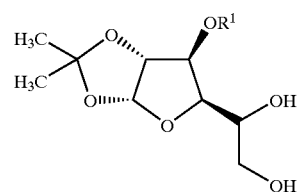

(4)

(c) reacting a compound of Formula (4) with a cleaving agent in a suitable solvent to form an aldehyde compound of Formula (5):

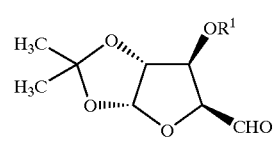

(5)

(d) reacting a compound of Formula (5) with a secondary amine compound of Formula (6):

$R^2R^3NH$ (6)

where $R^2$ and $R^3$ are as defined above, and a reducing agent in a suitable solvent followed by treatment with a reducing agent scavenger resin in a suitable solvent and an amine scavenger resin in a suitable solvent to form a tertiary amine compound of Formula (7).

33. A method for the synthesis of a compound of Formula (7'):

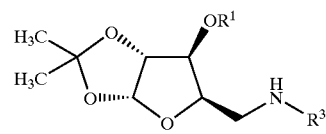

(7')

wherein:

$R^1$ is selected from the group consisting of —$C_{1-14}$alkyl and —$(CH_2)_{0-4}$-aryl; and $R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl;

which comprises the steps of:

(a) reacting a compound of Formula 1:

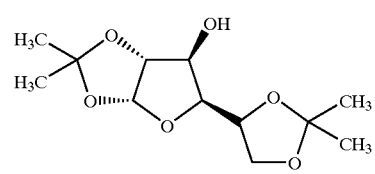

(1)

with an alkylating agent of Formula (2):

$R^1$—X (2)

in the presence of a deprotonation agent in a suitable solvent; where X is iodo or bromo and $R^1$ is as defined above, to yield an ether compound of Formula (3):

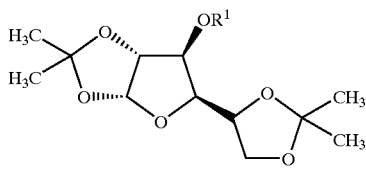
(3)

(b) reacting a compound of Formula (3) with a hydrolysing agent, to form a diol compound of Formula (4):

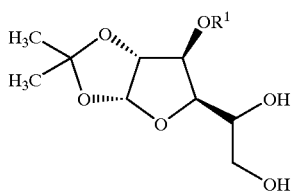
(4)

(c) reacting a compound of Formula (4) with a cleaving agent in a suitable solvent to form an aldehyde compound of Formula (5):

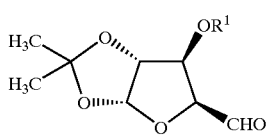
(5)

(d') reacting a compound of Formula (5) with a primary amine compound of Formula (6'):

$R^3NH_2$ (6')

where $R^3$ is as defined above, and a reducing agent in a suitable solvent followed by treatment with a reducing agent scavenger resin in a suitable solvent and an amine scavenger resin in a suitable solvent to form a secondary amine compound of Formula (7').

34. A method for the synthesis of a compound of Formula Ia:

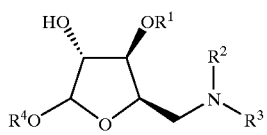
(Ia)

wherein:
$R^1$ is selected from the group consisting of —$C_{1-14}$alkyl and —$(CH_2)_{0-4}$-aryl;
$R^2$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl;
$R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^2$ and $R^3$ can be taken together with the nitrogen atom to which they are attached to form a heterocycloalkyl; and
$R^4$ is selected from the group consisting of H, —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl;

which comprises the step of:
(a) reacting a compound of Formula (7)

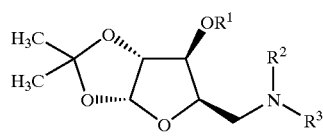
(7)

where $R^1$, $R^2$, and $R^3$ are as defined above, with a compound of Formula (8):

$R^4OH$ (8)

where $R^4$ is selected from the group consisting of H, —$C_{1-14}$alkyl, —$(CH_2)_{0-2}$-cycloalkyl, —$C_{2-6}$alkenyl, —$C_{2-8}$alkynyl and —$(CH_2)_{1-2}$-heterocycloalkyl, and an acid in a suitable solvent followed by treatment with an acid scavenger resin in a suitable solvent to form a compound of Formula Ia.

35. A method for the synthesis of a compound of Formula Ib:

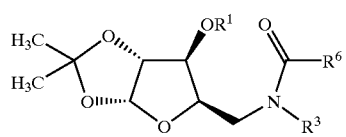
(Ib)

wherein:
$R^1$ is selected from the group consisting of —$C_{1-14}$alkyl and —$(CH_2)_{0-4}$-aryl;
$R^3$ is selected from the group consisting of —$C_{1-14}$alkyl, —$(CH_2)_{0-2}$—cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^6$ and $R^3$ can be taken together with the carbon and nitrogen atoms, respectively, to which they are attached to form a heterocycloalkyl containing an oxo (=O) substitution at the carbon atom; and
$R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-14}$-aryl;

which comprises the step of:
(a) reacting a compound of Formula (7')

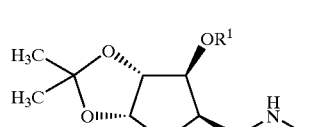
(7')

with an acid chloride compound of Formula (9):

$R^6COCl$ (9)

where $R^6$ is as defined above, and a suitable base in a suitable solvent followed by treatment with an acid chloride scavenger resin in a suitable solvent to form a compound of Formula Ib.

36. A method for the synthesis of a compound of Formula Ic:

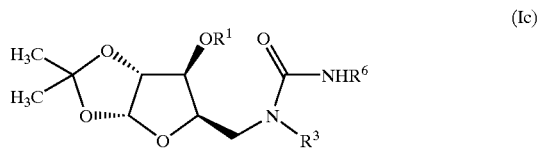

(Ic)

wherein:
- $R^1$ is selected from the group consisting of —$C_{1-14}$alkyl and —$(CH_2)_{0-14}$-aryl;
- $R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^6$ and $R^3$ can be taken together with the carbon and nitrogen atoms, respectively, to which they are attached to form a heterocycloalkyl containing an oxo (=O) substitution at the carbon atom; and
- $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

which comprises the steps of:
(a) reacting a compound of Formula (7')

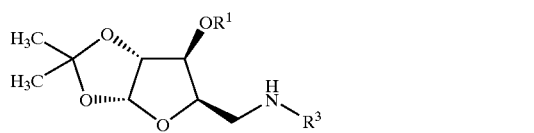

(7')

with an isocyanate compound of Formula (10):

$R^6NCO$ (10)

where $R^6$ is as defined above, in a suitable solvent followed by treatment with an isocyanate scavenger resin in a suitable solvent to form a compound of Formula Ic.

37. A method for the synthesis of an array compounds of Formula Ia:

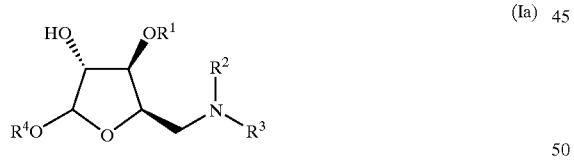

(Ia)

wherein:
- $R^1$ is selected from the group consisting of —$C_{1-14}$alkyl and —$(CH_2)_{0-4}$-aryl;
- $R^2$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl;
- $R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^2$ and $R^3$ can be taken together with the nitrogen atom to which they are attached to form a heterocycloalkyl; and
- $R^4$ is selected from the group consisting of H, —$C_{1-14}$ alkyl, —$(CH_2)_{0-2}$-cycloalkyl, —$C_{2-6}$alkenyl, —$C_{2-8}$alkynyl and —$(CH_2)_{1-2}$-heterocycloalkyl;

which comprises the step of:
(a) reacting an array of compounds of Formula (7)

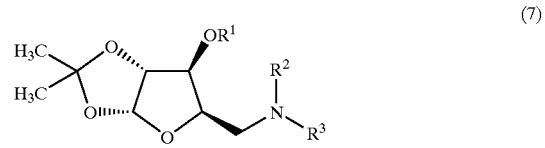

(7)

where $R^1$, $R^2$, and $R^3$ are as defined above, with an array of compounds of Formula (8):

$R^4OH$ (8)

where $R^4$ is selected from the group consisting of H, —$C_{1-14}$alkyl, —$(CH_2)_{0-2}$-cycloalkyl, —$C_{2-6}$alkenyl, —$C_{2-8}$-alkynyl and —$(CH_2)_{1-2}$-heterocycloalkyl, and an acid in a suitable solvent followed by treatment with an acid scavenger resin in a suitable solvent to form an array of compounds of Formula Ia.

38. A method for the synthesis of an array of compounds of Formula Ib:

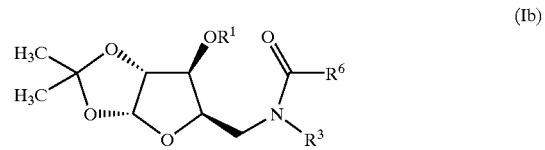

(Ib)

wherein:
- $R^1$ is selected from the group consisting of —$C_{1-14}$alkyl and —$(CH_2)_{0-4}$-aryl;
- $R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^6$ and $R^3$ can be taken together with the carbon and nitrogen atoms, respectively, to which they are attached to form a heterocycloalkyl containing an oxo (=O) substitution at the carbon atom; and
- $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

which comprises the step of:
(a) reacting an array of compounds of Formula (7')

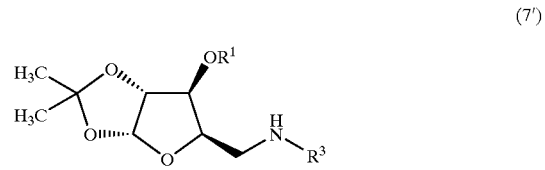

(7')

with an array of acid chloride compounds of Formula (9):

$R^6COCl$ (9)

where $R^6$ is as defined above, and a suitable base in a suitable solvent followed by treatment with an acid chloride scavenger resin in a suitable solvent to form an array of compounds of Formula Ib.

39. A method for the synthesis of an array of compounds of Formula Ic:

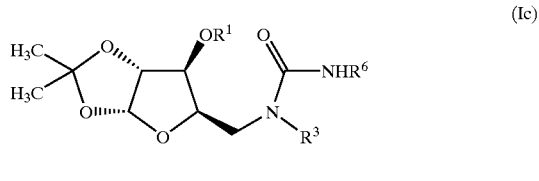
(Ic)

wherein:

$R^1$ is selected from the group consisting of —$C_{1-14}$alkyl and —$(CH_2)_{0-4}$-aryl;

$R^3$ is selected from the group consisting of —$C_{1-14}$alkyl, —$(CH_2)_{0-2}$-cycloalkyl, —$C_{2-6}$alkenyl, —$(CH_2)_{1-4}$-aryl, —$(CH_2)_{0-4}$-heterocycloalkyl, —$(CH_2)_{1-4}$-heteroaryl and —$(CH_2)_{0-2}$—O-aryl; or $R^6$ and $R^3$ can be taken together with the carbon and nitrogen atoms, respectively, to which they are attached to form a heterocycloalkyl containing an oxo (=O) substitution at the carbon atom; and $R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

which comprises the steps of:

(a) reacting an array of compounds of Formula (7')

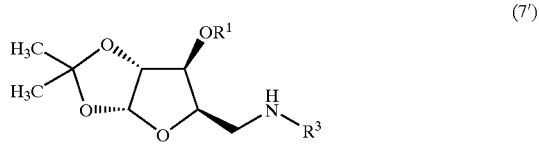
(7')

with an array of isocyanate compounds of Formula (10):

 $R^6NCO$ (10)

where $R^6$ is as defined above, in a suitable solvent followed by treatment with an isocyanate scavenger resin in a suitable solvent to form an array compounds of Formula Ic.

40. A method for the solid phase synthesis of a compound of Formula IIIa

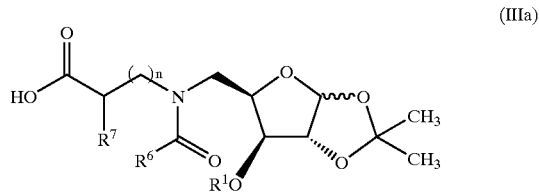
(IIIa)

wherein:

$R^1$ is selected from the group consisting of —$C_{1-14}$alkyl and —$(CH_2)_{0-4}$-aryl;

$R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

$R^7$ is an amino acid side chain; and n is an integer from 1–14;

which comprises the step of:

(a) reacting a compound of Formula (23)

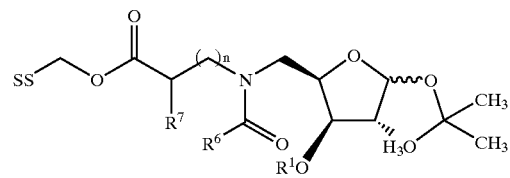
(23)

where SS is a solid support, and $R^1$, $R^6$, $R^7$, and n are as defined above, with an acid in a suitable solvent to form a compound of Formula IIIa.

41. The method according to Embodiment 40, wherein the acid is trifluoroacetic acid and the solvent is dichloromethane.

42. A method for the solid phase synthesis of a compound of Formula IIIb

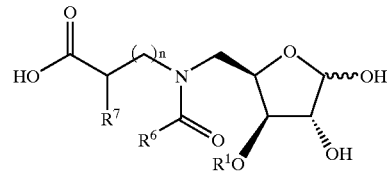
(IIIb)

wherein:

$R^1$ is selected from the group consisting of —$C_{1-14}$alkyl and —$(CH_2)_{0-4}$-aryl;

$R^6$ is selected from the group consisting of —$C_{1-4}$alkyl, —$(CH_2)_{0-2}$—O-aryl, —$C_{2-6}$alkenyl, —$(CH_2)_{0-2}$-cycloalkyl and —$(CH_2)_{1-4}$-aryl;

$R^7$ is an amino acid side chain; and n is an integer from 1–14;

which comprises the step of:

(a) reacting a compound of Formula (23)

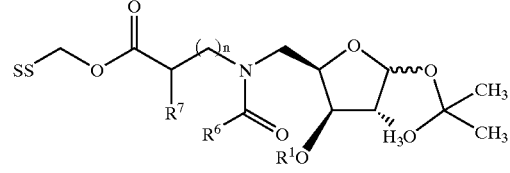
(23)

where SS is a solid support, and $R^1$, $R^6$, $R^7$, and n are as defined above, with an acid in an aqueous solvent to form a compound of Formula IIIb.

43. The method according to Embodiment 42 wherein the acid is trifluoroacetic acid.

44. A compound of Formula (7)

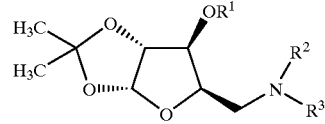
(7)

where $R^1$ is selected from the group consisting of —$C_{1-14}$alkyl and —$(CH_2)_{0-4}$-aryl;

R² is selected from the group consisting of —C₁₋₁₄alkyl, —(CH₂)₀₋₂-cycloalkyl, —C₂₋₆alkenyl, —(CH₂)₁₋₄-aryl, —(CH₂)₀₋₄-heterocycloalkyl, —(CH₂)₁₋₄-heteroaryl and —(CH₂)₀₋₂—O-aryl; and —R³ is selected from the group consisting of —C₁₋₁₄ alkyl, —(CH₂)₀₋₂-cycloalkyl, —C₂₋₆alkenyl, —(CH₂)₁₋₄-aryl, —(CH₂)₀₋₄-heterocycloalkyl, —(CH₂)₁₋₄-heteroaryl and —(CH₂)₀₋₂—O-aryl; or R² and R³ can be taken together with the nitrogen atom to which they are attached to form a heterocycloalkyl.

45. A compound of Formula (7')

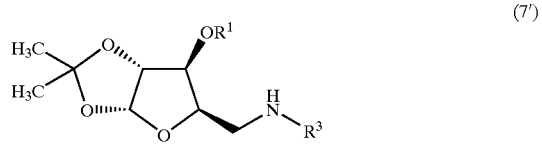

(7')

where
R¹ is selected from the group consisting of —C₁₋₁₄alkyl and —(CH₂)₀₋₄-aryl; and
R³ is selected from the group consisting of —C₁₋₁₄alkyl, —(CH₂)₀₋₂-cycloalkyl, —C₂₋₆alkenyl, —(CH₂)₁₋₄-aryl, —(CH₂)₀₋₄-heterocycloalkyl, —(CH₂)₁₋₄-heteroaryl and —(CH₂)₀₋₂—O-aryl, 46. A compound selected from:
4-Ethoxy-2-isopropoxy-5(4-phenyl-piperzin-1-ylmethyl)-tetrahydro-furan-3-ol;
5-[(Benzyl-phenethyl-amino)-methyl]-4-ethoxy-2-(2-methoxy-ethoxy)-tetrahydro-furan-3-ol;
4-Ethoxy-2-methoxy-5-(1,3,4,5-tetrahydro-pyrido[4,3-b]indol-2-ylmethyl)-tetrahydro-3-ol;
5-[4-(3-Chloro-phenyl)-piperazin-1-ylmethyl]-2-cyclopropylmethoxy-4-ethoxy-tetrahydro-furan-3-ol;
5-Dialkylaminomethyl-2-isobutoxy-4-(naphthalen-2-ylmethoxy)tetrahydro-furan-3-ol;
2-(3-Methoxy-3-methyl-butoxy)-5-morpholin-4-ylmethyl-4-(naphthalen-2-ylmethoxy)-tetrahydro-3-furan-3-ol;
5-[(Benzyl-methyl-amino)-methyl]-4-(naphthalen-2-yl methoxy)-2-pent-2-ynyloxy-tetrahydro-furan-3-ol;
4-Methoxy-5-(4-phenyl-piperazin-1-ylmethyl)-2-propoxy-tetrahydro-furan-3-ol;
2-Cyclopropylmethoxy-5-(3,4-dihydro-1H-isoquinolin-2-ylmethyl)-4-methoxy-tetrahydro-furan-3-ol;
5-[(Benzyl-methyl-amino)-methyl]-4-methoxy-2-pent-2-ynyloxy-tetrahydro-furan-3-ol;
4-Butoxy-2-(2-methoxy-ethoxy)-5-[(methyl-phenethyl-amino)-methyl]-tetrahydro-furan-3-ol;
4-Butoxy-2-methoxy-5-(1,3,4,5-tetrahydro-pyrido[4,3-b]indol-2-ylmethyl)-tetrahydro-furan-3-ol;
4-(3-Methoxy-benzyloxy)-2-(3-methoxy-3-methyl-butoxy)-5-morpholin-4-ylmethyl-tetrahydro-furan-3-ol;
5-Dialkylaminomethyl-2-isobutoxy-4-(3-methoxy-benzyloxy)-tetrahydro-furan-3-ol; and
5-[(Dibenzylamino)-methyl]-2-ethoxy-4-(3-methoxy-benzyloxy)-tetrahydro-furan-3-ol.

47. A compound selected from:
Cyclohexanecarboxylic acid (6-benzyloxy-2,2-dimethyl-tetrahydro-furo[2,3-d][1,3]dioxol-5-ylmethyl)-(2-diethylamino-ethyl)-amide;
N-(6-Benzyloxy-2,2-dimethyl-tetrahydro-furo[2,3-d][1,3]dioxol-5-ylmethyl)-N-(2-methoxy-benzyl)-2,2-diphenyl-acetamide;
N-Butyl-N-[6-(3-methoxy-benzyloxy)-2,2-dimethyl-tetrahydro-furo[2,3-d][1,3]dioxol-5-ylmethyl]-benzamide;
N-(2,4-Dimethoxy-benzyl)-N-(6-methoxy-2,2-dimethyl-tetrahydro-furo[2,3-d][1,3]dioxol-5-ylmethyl)-2,2-diphenyl-acetamide;
Cyclohexanecarboxylic acid (6-benzyloxy-2,2-dimethyl-tetrahydro-furo[2,3-d][1,3]dioxol-5-ylmethyl)-(3-methoxy-propyl)-amide; and
N-(1-Benzyl-pyrrolidin-3-yl)-N-[6-(3-methoxy-benzyloxy)-2,2-dimethyl-tetrahydro-furo[2,3-d][1,3]dioxol-5-ylmethyl]-benzamide.

48. A compound selected from:
1-Benzyl-3-ethyl-1-(6-methoxy-2,2-dimethyl-tetrahydro-furo[2,3-d][1,3]dioxol-5-ylmethyl)-urea;
1-(6-Methoxy-2,2-dimethyl-tetrahydro-furo[2,3-d][1,3]dioxol-5-ylmethyl)-3-phenyl-1-(4-trifluoromethoxy-benzyl)-urea;
1-Cyclopropylmethyl-3-isopropyl-1-[6-(3-methoxy-benzyloxy)-2,2-dimethyl-tetrahydro-furo[2,3-d][1,3]dioxol-5-ylmethyl]-urea;
3-Ethyl-1-(6-methoxy-2,2-dimethyl-tetrahydro-furo[2,3-d][1,3]dioxol-5-ylmethyl)-1-phenethyl-urea;
1-(6-Benzyloxy-2,2-dimethyl-tetrahydro-furo[2,3-d][1,3]dioxol-5-ylmethyl)-3-ethyl-1-[2-(1H-indol-2-yl)-ethyl]-urea; and
1-Allyl-1-[6-(3-methoxy-benzyloxy)-2,2-dimethyl-tetrahydro-furo[2,3-d][1,3]dioxol-5-ylmethyl]-3-phenyl-urea.

49. A compound selected from:
N-(4,5-Dihydroxy-3-methoxy-tetrahydro-furan-2-ylmethyl)-N-(2-methoxy-benzyl)-2,2-diphenyl-acetamide; and
N-Butyl-N-[4,5-dihydroxy-3-(3-methoxy-benzyloxy)-tetrahydro-furan-2-ylmethyl]-benzamide.

50. A compound named 1-(3-benzyloxy-4,5-dihydroxy-tetrahydro-furan-2-ylmethyl)-3-phenyl-1-(4-trifluoromethoxy-benzyl)-urea.

Experimental Details

Scheme I below further illustrates the method of the present invention for preparing an individual compound or an array of compounds of Formula 5.

Scheme I

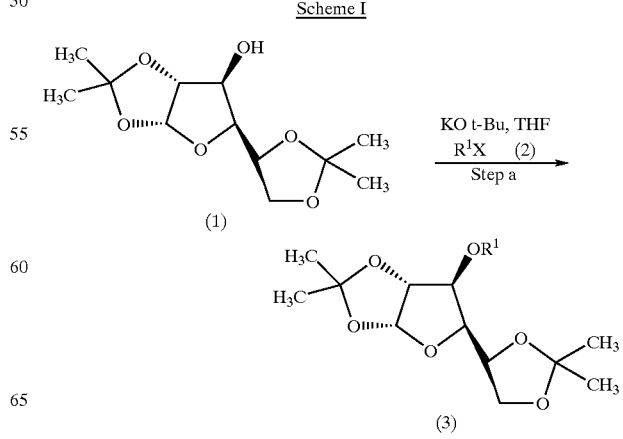

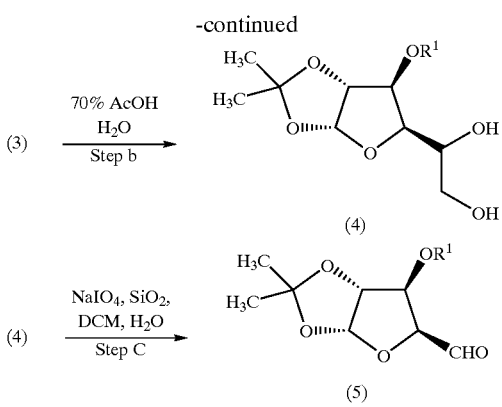

where R[1] is as defined above.

Compounds of Formula 1 and Formula 2 and other reactants used in Scheme I are available from commercial sources or can be synthesized by using techniques known to one skilled in the art.

Step (a), Formula 3 (Alkylation of Diacetone D-Glucose with Iodoethane)

Formula 3a (Formula 3 where R[1] is —CH$_2$CH$_3$): A flask was charged with DMSO (545 mL) and finely ground potassium hydroxide (73.4 g, 1.3 mol, 4 equiv). The mixture was stirred until 90% homogeneous (about 20 min). The solution was cooled to an internal temperature of 10° C., and diacetone D-glucose (Formula 1, 85.1 g, 0.327 mol, 1.0 equiv) was added in a single portion. The mixture was allowed to stir for 30 min. Iodoethane (Formula 2, 52 mL, 0.654 mol, 2.0 equiv) was added over 20 min, and the internal temperature was kept below 30° C. Following addition of iodoethane, the reaction was allowed to reach ambient temperature and was stirred overnight (about 14 hours). The opaque brown solution was checked by TLC (1:1 hexane/ether, anisaldehyde stain) and was judged complete. The completed reaction was diluted with water (320 mL) and extracted twice with Et$_2$O (1×300 mL, 1×150 mL). The organic layers were combined, washed with saturated aqueous NaCl (200 mL), and dried over sodium sulfate. The organic layers were filtered, concentrated in vacuo, and dried under high vacuum to afford 80.4 g (85%) of the acetonide of Formula 3a, a pale yellow oil that was used in the next step.

Formula 3b (Formula 3 where R[1] is —(CH$_2$)$_4$CH$_3$): Following analogous procedures, the acetonide of Formula 3b (87%) was obtained.

Formula 3c (Formula 3 where R[1] is —CH$_2$—C$_{10}$H$_7$): Following analogous procedures, the acetonide of Formula 3c (quantitative) was obtained. Dichloromethane was used instead of Et$_2$O as the workup solvent for extracting the aqueous layers.

Formula 3d (Formula 3 where R[1] is —(CH$_2$)$_3$CH$_3$): Following analogous procedures, the acetonide of Formula 3d was obtained.

Step (a), Formula 3 (Alkylation of Diacetone D-Glucose with 3-Methoxybenzyl Bromide)

Formula 3e (Formula 3 where R[1] is 3-methoxy-phenyl): Diacetone D-glucose (Formula 1, 15.0 g, 57.6 mmol) was dissolved in anhydrous THF (115 mL, 0.5 M) under nitrogen. While vigorously stirring at ambient temperature, a solution of KO t-Bu in THF (69 mL, 69 mmol, 1 M, Aldrich) (Yu, et al., Org. Process Res. Dev. 3:53–55, 1999) was added in one portion. The solution color slowly changed from colorless to bright yellow. After stirring at ambient temperature for 14 hours under nitrogen, 3-methoxybenzyl bromide (9.7 mL, 69 mmol, Aldrich) was added and a tan precipitate formed. After an additional 24 hours, the reaction was judged complete by TLC (1:1 hexane/EtOAc). The reaction was quenched with water (200 mL) and diluted with Et$_2$O (200 mL). After separation of the organic and aqueous layers, the aqueous layer was extracted with Et$_2$O (3×200 mL). The combined organic layers were washed with saturated aqueous NaCl, dried over anhydrous MgSO$_4$ for 30 min, filtered, and concentrated in vacuo to yield 19.3 g (88%) of the crude acetonide of Formula 3e as a pale yellow oil.

Formula 3f (Formula 3 where R[1] is —CH$_2$—C$_6$H$_5$): Following analogous procedures, the acetonide of Formula 3f (88%) was obtained.

Formula 3g (Formula 3 where R[1] is —CH$_3$): For the synthesis of the acetonide of Formula 3g, dimethyl sulfate was used as the alkylating agent and potassium bromide salt did not precipitate out of the reaction mixture. In this reaction, addition of dimethyl sulfate caused the reaction mixture to become a gel-like suspension that subsequently became homogeneous after stirring.

Step (b), Formula 4 (Hydrolysis to the Diol)

Formula 4a (Formula 4 where R[1] is —CH$_2$CH$_3$): Acetonide (Formula 3a, 80.4 g, 279 mmol) was dissolved in aqueous AcOH (560 mL, 70%, v/v, 0.5 M). After stirring at ambient temperature for 14 hours, the reaction was judged complete by TLC (1:1 hexane/EtOAc, anisaldehyde stain). Solvent was removed in vacuo (<35° C.), followed by azeotroping with toluene (2×200 mL) to afford crude yellow oil. The crude oil was dissolved in water (250 mL) and the aqueous layer was extracted with hexane (2×200 mL). The aqueous layer was extracted with DCM (3×200 mL) and dried over magnesium sulfate. The organic layers were filtered and concentrated in vacuo to yield 47.7 g (69%) of the diol of Formula 4a as a colorless oil.

Formula 4b (Formula 4 where R[1] is —(CH$_2$)$_4$CH$_3$): Following analogous procedures, the diol of Formula 4b (85%) was obtained.

Formula 4c (Formula 4 where R[1] is —CH$_2$—C$_{10}$H$_7$): Following analogous procedures, the diol of Formula 4c (quantitative) was obtained.

Formula 4d (Formula 4 where R[1] is —(CH$_2$)$_3$CH$_3$): Following analogous procedures, the diol of Formula 4d (86%) was obtained.

Formula 4e (Formula 4 where R[1] is 3-methoxy-phenyl): Following analogous procedures, the diol of Formula 4e (93%) was obtained.

Formula 4f (Formula 4 where R[1] is —CH$_2$—C$_6$H$_5$): Following analogous procedures, the diol of Formula 4f (89%) was obtained.

Formula 4g (Formula 4 where R[1] is —CH$_3$): Following analogous procedures, the diol of Formula 4g (90%) was obtained.

Step (c), Formula 5 (Synthesis of Aldehyde)

Formula 5a (Formula 5 where R[1] is —CH$_2$CH$_3$): Silica gel (80.6 g, EM Science, catalog no. 9385-9) was suspended in DCM (806 mL). An aqueous solution of sodium periodate (80.6 mL, 52.3 mmol, 0.65 M) was added dropwise over 5 min and a white precipitate formed. A solution of the diol (Formula 4a, 10.0 g, 40.3 mmol, 0.5 M) in DCM (80.6 mL) was added in one portion to the flask. After stirring at ambient temperature for 1.5 hours, the reaction was judged complete by TLC (1:1 hexane/EtOAc, anisaldehyde stain). The reaction was diluted with water (275 mL). The aqueous and organic layers were separated and the aqueous layer was extracted with DCM (3×75 mL). The combined organic layers were dried over magnesium sulfate, filtered, and concentrated in vacuo to yield a colorless oil that was dried under high vacuum for 12 hours to afford 6.4 g (57%) of the aldehyde of Formula 5a. The aldehyde can be stored for 3–5 days under high vacuum prior to use in the next step.

$^1$H NMR (270 MHz, CDCl$_3$) δ 9.66 (d, J=1.5 Hz, 1H), 6.11 (d, J=3.5 Hz, 1H), 4.60 (d, J=3.3 Hz, 1H), 4.54 (dd, J=2.0, 2.0 Hz, 1H), 4.22 (d, J=3.8 Hz, 1H), 3.67–3.56 (m, 1H), 3.51–3.39 (m, 1H), 1.48 (s, 3H), 1.34 (s, 3H), 1.36 (t, J=7.2 Hz, 3H).

Formula 5b (Formula 5 where R$^1$ is —(CH$_2$)$_4$CH$_3$): Following analogous procedures, the aldehyde of Formula 5b (83%) was obtained.

$^1$H NMR (270 MHz, CDCl$_3$) δ 9.65 (d, J =1.7 Hz, 1H), 6.11 (d, J=3.5 Hz, 1H), 4.59 (d, J=3.5 Hz, 1H), 4.54 (dd, J=3.8, 1.8 Hz, 1H), 3.54 (ddd, J=9.3, 6.8, 6.8 Hz, 1H), 3.37 (ddd, J=9.3, 6.5, 6.5 Hz, 1H), 1.56–1.42 (m, 2H), 1.48 (s, 3H), 1.34 (s, 3H), 1.22 (m, 5H), 0.87 (t, J=6.8 Hz, 3H).

Formula 5c (Formula 5 where R$^1$ is —CH$_2$—C$_{10}$H$_7$): Following analogous procedures, the aldehyde of Formula 5c (99%) was obtained.

$^1$H NMR (270 MHz, CDCl$_3$) δ 9.71 (d, J=1.5 Hz, 1H), 7.87–7.77 (m, 3H), 7.52–7.41 (m, 3H), 7.35 (dd, J=8.5, 1.8 Hz, 1H), 6.15 (d, J=3.5 Hz, 1H), 4.76 (dd, J=4.5 Hz, 1H), 4.67 (dd, J=5.8, 3.5 Hz, 2H), 4.58 (dd, J=3.8, 1.5 Hz, 1H), 4.39 (d, J=3.8 Hz, 1H), 1.47 (s, 3H), 1.34 (s, 3H).

Formula 5d (Formula 5 where R$^1$ is —(CH$_2$)$_3$CH$_3$): Following analogous procedures, the aldehyde of Formula 5d (99%) was obtained.

$^1$H NMR (270 MHz, CDCl$_3$) δ 9.65 (d, J=1.7 Hz, 1H), 6.10 (d, J=3.5 Hz, 1H), 4.60 (d, J=3.5 Hz, 1H), 4.54 (dd, J=3.8, 1.8 Hz, 1H), 4.19 (d, J=3.9Hz, 1H), 3.56 (ddd, J=9.3, 6.5, 6.5 Hz, 1H), 3.39 (dd, J=9.3, 6.5, 6.5 Hz, 1H), 1.48 (s, 3H), 1.47 (dddd, J=7.3, 1.5, 1.5 Hz, 2H), 1.34 (s, 3H), 1.31 (dddd, J=15.1, 5.8, 5.8 Hz, 2H), 0.88 (t, J=7.4 Hz, 3H).

Formula 5e (Formula 5 where R$^1$ is 3-methoxy-phenyl): Following analogous procedures, the aldehyde of Formula 5e (81%) was obtained.

$^1$H NMR (270 MHz, CDCl$_3$) δ 9.68 (d, J=1.7 Hz, 1H), 7.24 (t, J=7.6 Hz, 1H), 6.89–6.75 (m, 3H), 6.13 (d, J=3.4 Hz, 1H), 4.65–4.56 (m, 3H), 4.47 (s, 1H), 4.32 (d, J=3.7 Hz, 1H), 3.80 (s, 3H), 1.26 (s, 3H).

Formula 5f (Formula 5 where R$^1$ is —CH$_2$—C$_6$H$_5$): Following analogous procedures, the aldehyde of Formula 5f (87%) was obtained.

$^1$H NMR (270 MHz, CDCl$_3$) δ 9.62 (d, J=1.4 Hz, 1H), 7.31–7.17 (m, 5H), 6.07 (d, J=3.4 Hz, 1H), 4.59 (d, J=3.4 Hz, 2H), 4.52 (dd, J=3.7, 1.5 Hz, 1H), 4.45 (s, 1H), 4.40 (s, 1H), 4.29 (d, J=3.7 Hz, 1H), 1.41 (s, 3H), 1.26 (s, 3H).

Formula 5g (Formula 5 where R$^1$ is —CH$_3$): Following analogous procedures, the aldehyde of Formula 5g (66%) was obtained.

$^1$H NMR (270 MHz, CDCl$_3$) δ 9.62 (d, J=1.5 Hz, 1H), 6.07 (d, J=3.7 Hz, 1H), 4.61 (d, J=3.7 Hz, 1H), 4.53 (dd, J=3.7, 1.7 Hz, 1H), 4.10 (d, J=3.7 Hz, 1H), 3.33 (s, 3H), 1.46 (s, 3H), 1.32 (s, 3H).

Scheme Ia below further illustrates the method of the present invention for preparing an individual compound or an array of compounds of Formula Ia.

Scheme Ia (5) 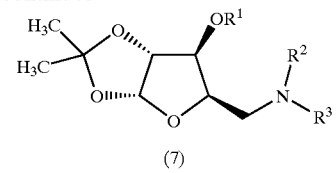
1) R$^2$R$^3$NH (6), NaBH(OAc)$_3$, 1,4-Dioxane
2) Amberlite IRA-743 resin, 1,4-Dioxane
3) SS-Isocyanate resin, 1,4-Dioxane
──────────────→
Step d -continued

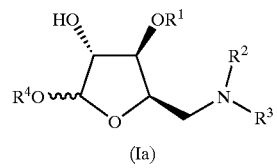
(7)

(7) 1) R$^4$OH (8), 4M HCl in 1,4-Dioxane
2) SS-Methylpiperidine resin, 1,4-Dioxane
──────────────→
Step e (Ia)

where R$^1$, R$^2$, R$^3$ and R$^4$ are as defined above.

Compounds of Formula 6 and Formula 8 and other reactants used in Scheme Ia are available from commercial sources or can be synthesized by using techniques known to one skilled in the art.

Step (d), Formula 7

1) Preparation of Aldehyde/Amine Solutions, Plating of NaBH(OAc)$_3$ and Reductive Amination 0.25 M stock solutions of each aldehyde was prepared by diluting the amount to a total volume of 1.8 L with 1,4-dioxane. Each reducing amine (6.325 mmol, 1.1 equiv) was weighed and treated with the appropriate aldehyde solution (23 mL, 5.75 mmol, 1.0 equiv).

Plates were filled to capacity with powdered NaBH(OAc)$_3$ (70–80 mg/well, 0.30 mmol, 1.5 equiv) (Abdel-Magid, et al., *Tetrahedron Lett.* 31:5595–5598, 1990; Abdel-Magid, et al., *J. Org. Chem.* 61:3849–3862, 1996; and Love, et al., *Organic. Preparations and Procedures Int.* 4:399–405, 1999). The appropriate amine/aldehyde solution (0.80 mL/well) was transferred to each well of the plates, which were then sealed and agitated for about 7–14 hours at ambient temperature (22–27° C.).

2) Removal of Borate

Washing of the Amberlite IRA-743 resin (Aldrich catalog no. 21,664–5) was performed one day before the reductive amination reaction was complete to ensure thorough dryness of the resin. Amberlite IRA-743 resin (150 g), used to selectively remove borate salts, was weighed and combined with absolute EtOH (100 mL, 200 proof) (Hicks, et al., *Carbohydrate Research* 147:39–48, 1986; Repic, "3.2.4 Minimization of Boron Content" in *Principles of Process Research and Chemical Development in the Pharmaceutical Industry*, Wiley: New York, N.Y., pp71–74, 1998). The resin slurry was stirred and the EtOH solution was filtered under vacuum for 5 min. This process was repeated twice. After the second EtOH wash, the resin was dried under vacuum until it was free flowing and no longer sticky (about 1 hour). Plate wells were filled to capacity with the washed Amberlite resin (400–500 mg/well). After 7 hours, the contents of the plates from Step (d)1 were diluted with anhydrous, inhibitor-free THF (500 μL/well) and agitated for an additional 30 min. The contents of the wells were transferred to the corresponding wells of the plates packed with washed Amberlite resin. The plates were rinsed with 1,4-dioxane (2×250 μL/well), and the rinse was transferred to the appropriate wells of the Amberlite resin-containing plates. Upon complete transfer, the Amberlite resin-containing plates were agitated for at 14–72 hours (22–27° C.).

3) Removal of Excess Secondary Amine

The wells of a plate were filled to capacity with SS-Isocyanate resin (Argonaut, catalog no. 800262, lot no. 00989, loading 1.49 mmol/g, 200–225 mg/well). After a reaction period of 14–72 hours, the plates from Step (d)2 were frozen in dry ice for 15 min, then transferred to the top of the SS-Isocyanate resin-containing plates (200 mg/well), and allowed to drain for at least 45–60 min. The resins were washed with 1,4-dioxane (2×0.25 mL/well, 5 min between washes), allowing the washes to be collected into the bottom plates. After complete drainage, the bottom plates were agitated for 14–72 hours (22–27° C.). After at least 14 hours, the plates were frozen in dry ice for 15 min, and allowed to drain for at least 45–60 min. The resins in the were washed with 1,4-dioxane (2×0.25 mL/well, 5 min between washes), and the washes were collected. After complete drainage, the plates were sampled for completeness of reaction. After sampling, the plates were frozen for at least 1 hour at −80° C. and lyophilized for at least 18 hours. If the desired product was present at >80% (AUC at 214 nm), the next step was performed.

Step (e), Formula Ia

1) Acetonide Hydrolysis/Mixed Acetal Formation

Solutions of the desired primary alcohol/4 M HCl in dioxane (1:1, v/v) were prepared in by diluting the amount given for each alcohol (65 mL) to a final volume of 130 mL with 4 M HCl in 1,4-dioxane. The lyophilized plates from Step (d) were treated with the alcohol/4 M HCl in 1,4-dioxane solutions (1.5 mL/well). Once all wells were treated, the plates were sealed and agitated for 14–18 hours at ambient temperature (22–27° C.). After 14 hours, the plates were placed under vacuum at medium to high heat for 3–5 hours.

2) Scavenging of Excess Acids

Plate wells were filled to capacity with SS-Piperidine resin (Polymer Labs, PL-PIP catalog no. 3410–4679, lot no. BT/107/189, loading 3.1 mmol/g, 200 mg/well). The contents of the plates from Step (e)1 were dissolved in a 5:1 solution of 1,4-dioxane/anhydrous, inhibitor-free THF (1.5 mL/well) and transferred to the plates containing the SS-piperidine resin. The plates were then agitated at ambient temperature (22–27° C.) for 14–72 hours. After at least 14 hours, the plates were frozen in dry ice for 15 min, and allowed to drain for 45–60 min. The resins in the plates were washed with 1,4-dioxane (2×0.50 ml/well, 5 min between each rinse). After draining, the plates were sampled for completeness of reaction. After sampling, the plates were frozen for at least 1 hour at −80° C. and lyophilized for at 14–72 hours.

Scheme Ib below further illustrates the method of the present invention for preparing an individual compound or an array of compounds of Formula Ib.

Scheme Ib

1) R$^3$NH$_2$ (6'), NaBH(OAc)$_3$, EtOH
2) Amberlite IRA-743 resin, EtOH
3) SS-4-Benzyloxybenzaldehyde resin, 1,4-Dioxane (5) $\xrightarrow{\text{Step d'}}$

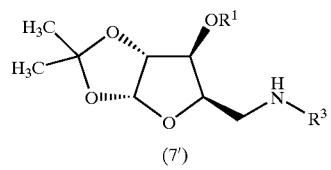

(7')

-continued

1) R$^6$COCl (9), NMM in 1,4-Dioxane
2) SS-Methylpiperidine resin, 1,4-Dioxane (7') $\xrightarrow{\text{Step e'}}$

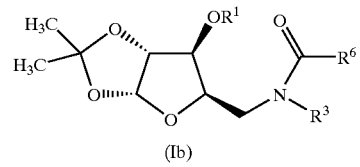

(Ib)

where R$^3$ and R$^6$ are as defined above.

Compounds of Formula 6' and Formula 9 and other reactants used in Scheme Ib are available from commercial sources or can be synthesized by using techniques known to one skilled in the art.

Step (d'), Formula 7'

1) Reductive Amination

The primary amines (Formula 6') were prepared and placed in bottles. 0.25 M stock solutions of the desired aldehydes (Formula 5) were prepared by diluting to a total volume of 1056 mL with absolute EtOH (200 proof). Each amine-containing bottle was treated with the appropriate 0.25 M solution of aldehyde 30 mL, 7.5 mmol, 1 equiv.) in absolute EtOH (200 proof), followed by treatment with neat reducing amine (23 mmol, 3 equiv.). NaBH(OAc)$_3$ (2.07 g, 9.75 mmol, 1.3 equiv.) was quickly added to each bottle. The bottles were sealed and agitated at ambient temperature (22–27° C.) for 5–7 hours.

2) Removal of Borate

Amberlite IRA-743 resin (150 g) was washed as described in Step (d)2. The resin was then weighed out into 15 g batches and transferred into the bottles from Step (d')1 (15 g/bottle), and agitated for at least 14 hours at ambient temperature (22–27° C.). After at least 14 hours, the contents of each bottle were filtered into flasks. The resin was washed with additional absolute EtOH (200 proof) (2×30 mL, 5 min between washes), and the washes collected into flasks. The contents of the flasks were concentrated to dryness.

3) Removal of Excess Primary Amine

The concentrated material from Step (d')2 was diluted with DCM (260 mL) and transferred to bottles containing 4-benzyloxybenzaldehyde solid supported scavenger resin (14 g/bottle, unwashed, Midwest Biotech, Catalog No. 20815, 1 g/mmol amine) (Kaldor, et al., *Tetrahedron Lett.* 37:7193–7196, 1996; Hodges, *Synlett.* 1:152–158, 1999). The bottles were sealed and agitated for at least 14 hours at ambient temperature (22–27° C.). After at least 14 hours, the contents of each bottle was filtered into a flask. The resins were washed with DCM (2×50 mL, 5 min between washes) and collected in the flask. The contents of the flasks were concentrated to dryness.

Step (e'), Formula Ib

1) Secondary Amine Plating, Preparation of Acid Chloride Solutions, and Acylation with Acid Chlorides The secondary amines (Formula 7') of Step (d')3 were diluted with 1,4 dioxane to a final concentration of 0.5 M. 0.6 M solutions of the desired acid chloride (Formula 9) in 0.75 M NMM in 1,4-dioxane were prepared. Each plate well was then treated with 0.5 M solution of appropriate secondary amine (0.2 mL/well, 0.1 mmol, 1 equiv.) and the 0.6 M acid chloride solution (0.2 mL, 0.12 mmol, 1.2 equiv.). The plates were sealed and agitated for at least 3 hours at ambient temperature (22–27° C.). After at least 3 hours, the contents of the wells were treated with water (0.02 mL/well, 1.11 mmol, 11 equiv.), then resealed and agitated for 1 hour.

2) Scavenging of Excess Acid Chlorides

Plate wells were filled completely with 100 mg/well of the sticky DOWEX anion exchange resin (SBr LC NG OH form, Supelco, #14036-U) (Gayo, et al., *Tetrahedron Lett.* 38:513–516, 1997; Booth, et al, *Acc. Chem. Res.* 32:18–26, 1999). The resin was then washed with MeOH (2×1.0 mL/well, 5 min between washes). After 1 hour, the contents of the wells from Step (e')1 were diluted with 1,4-dioxane (0.250 mL/well) and the contents transferred to the Dowex anion exchange resin-containing plates. The plates were sealed and agitated for at least 14 hours at ambient temperature (22–27° C.). After 14 hours of reaction time, the plates were frozen in dry ice for 10–15 min, and then allowed to drain for 45 min. The contents of the plates were rinsed with 1,4-dioxane 0.5 mL/well (2×0.25 mL with 1 min between rinses) and collected. The plates were then frozen at –80° C. for 1 hour, after which they were lyophilized for at least 14 hours.

Scheme Ic below further illustrates the method of the present invention for preparing an individual compound or an array of compounds of Formula Ic.

Scheme Ic

1) $R^6$NCO (10), 1,4-Dioxane
2) SS-Tris(2-aminoethyl)amine resin, 1,4-Dioxane (7')  $\xrightarrow{\text{Step e''}}$

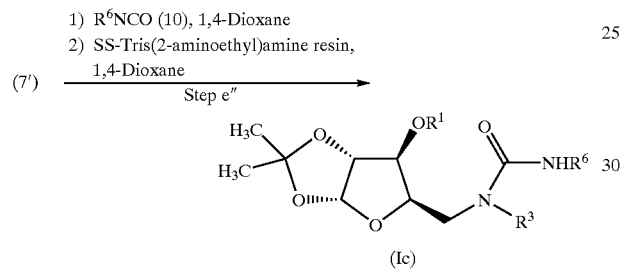

(Ic)

where $R^6$ is as defined above.

Compounds of Formula 10 and other reactants used in Scheme Ic are available from commercial sources or can be synthesized by using techniques known to one skilled in the art.

Step (e") Formula Ic

1) Secondary Amine Plating, Preparation of Isocyanate Solutions, and Acylation with Isocyanates The secondary amines (Formula 7') of Step (d')3 were diluted with 1,4 dioxane to a final concentration of 0.5 M. 0.6 M solutions of the desired isocyanate (Formula 10) in 1,4-dioxane were prepared. Each plate well was then treated with 0.5 M solution of appropriate secondary amine (0.2 mL/well, 0.1 mmol, 1 equiv.) and the 0.6 M isocyanate solution (0.2 mL, 0.12 mmol, 1.2 equiv.). The plates were sealed and agitated for at least 3 hours at ambient temperature (22–27° C.). After at least 3 hours, the contents of the wells were treated with water (0.02 mL/well, 1.11 mmol, 11 equiv.), then resealed and agitated for 3 hours.

2) Scavenging of Excess Isocyanates

Plate wells were filled completely with 0.075 g/well of the tris(2-aminoethyl)amine scavenger resin (Midwest Biotech, Catalog No. 20920) (Weidner, et al., *Tetrahedron Lett.* 40:239–242, 1999; Kaldor, et al., *Tetrahedron Lett.* 37: 7193–7196, 1996). After 3 hours, the contents of the wells from Step (e")1 were diluted with 1,4-dioxane (0.250 mL/well) and the contents transferred to the tris(2-aminoethyl)amine scavenger resin-containing plates. Then plates from Step (e")1 were rinsed with 0.50 mL/well 1,4-dioxane (2×0.250 mL with 1 min between rinses), and the solutions transferred to the appropriate wells in the resin-containing plates. The plates were sealed and agitated for at least 14 hours at ambient temperature (22–27° C.). After 14 hours of reaction time, the plates were frozen in dry ice for 10–15 min, and then allowed to drain for 45 min. The contents of the plates were rinsed with 1,4-dioxane 0.5 mL/well (2×0.25 mL with 1 min between rinses) and collected. The plates were then frozen at –80° C. for 1 hour, after which they were lyophilized for at least 14 hours.

Schemes IIa–c below further illustrates the method of the present invention for preparing an individual compound or an array of compounds of Formulas IIa, IIb and IIc, where $R^1$, $R^3$ and $R^6$ are as defined above.

Scheme IIa

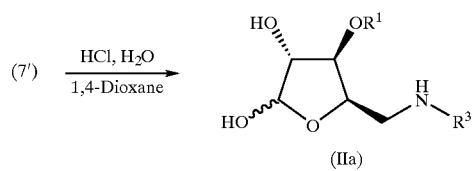

(IIa)

Scheme IIb

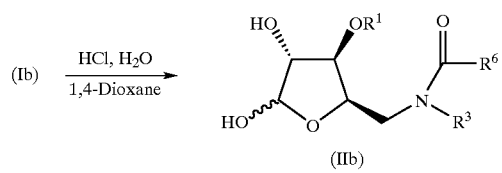

(IIb)

Scheme IIc

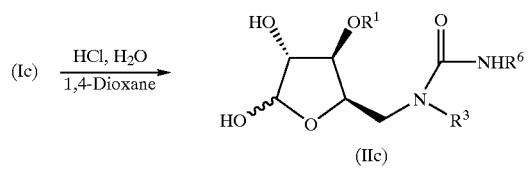

(IIc)

Scheme II-Acetonide Hydrolysis, Formulas IIa, IIb and IIc

Each acetonide was treated with a 1:1 mixture (v/v) of 4M HCl in 1,4-dioxane/water (1.00 mL/well). The plate was agitated for at least 24 hours at ambient temperature. After at least 14 hours, the plate was frozen and lyophilized to yield the desired hemi acetals.

Along with the solution phase route of synthesis described in Schemes Ia, Ib and Ic, the related compounds of Formula III can also be synthesized by solid-phase routes, two such routes being exemplified below Scheme IIIa

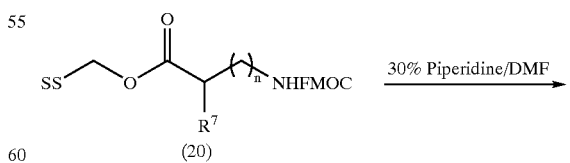

(20)

$\xrightarrow{\text{30\% Piperidine/DMF}}$

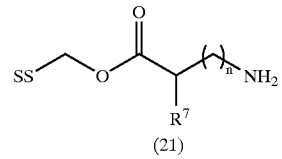

(21)

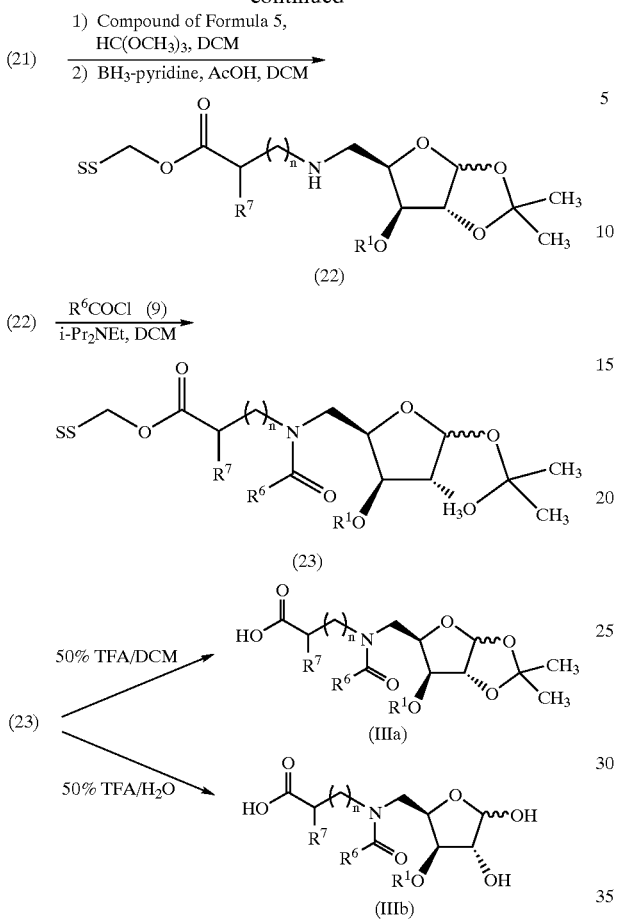

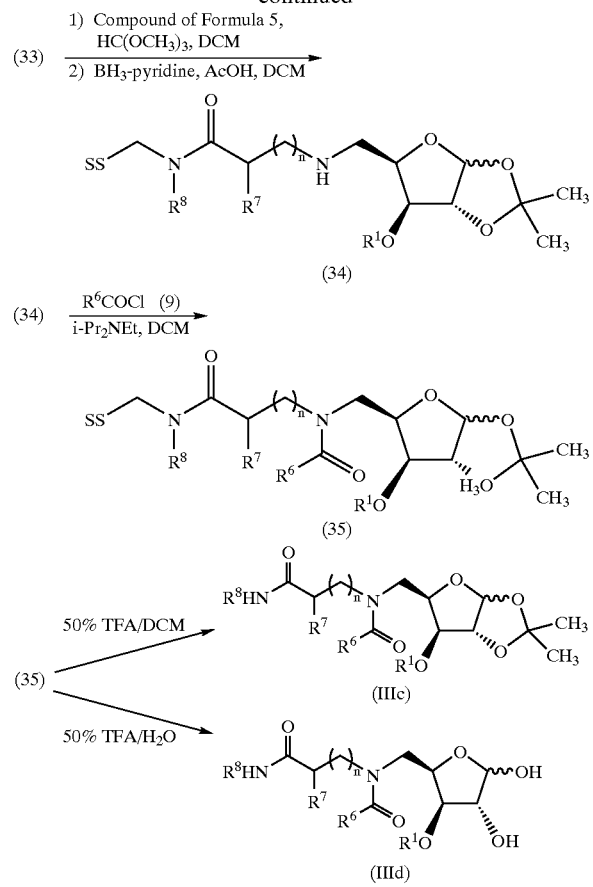

SS is a solid support and $R^1$, $R^6$, $R^7$ and n are as defined above. Compounds of Formula 20 and other reactants used in Scheme IIIa are available from commercial sources or can be synthesized by using techniques known to one skilled in the art.

Scheme IIIb

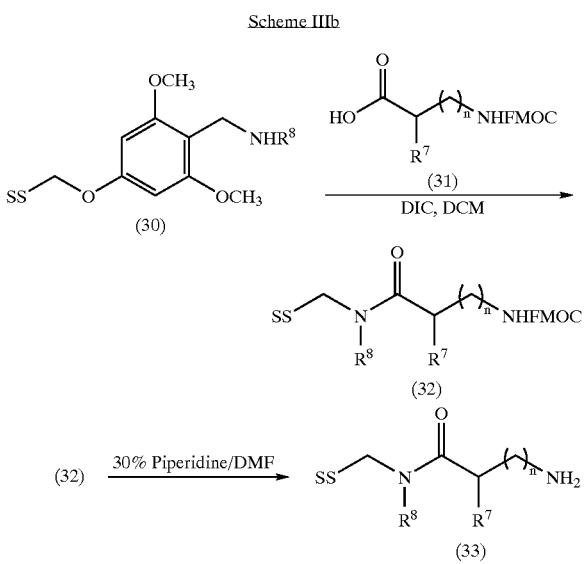

SS is a solid support $R^1$, $R^6$, $R^7$, $R^8$ and n are as defined above. Compounds of Formula 30 and other reactants used in Scheme IIIb are available from commercial sources or can be synthesized by using techniques known to one skilled in the art.

EXAMPLES

The invention is further illustrated by way of the following examples, which are intended to enable those skilled in the art to more clearly understand and to practice the present invention. These examples illustrate the synthesis of representative examples of compounds of Formula I that were prepared using the method of the present invention. These examples are not intended, nor are they to be construed, as limiting the scope of the invention, but are merely illustrative and representative thereof. It should be understood that all of the parts, percentages, and proportions referred to herein and in the appended claims are by weight unless otherwise indicated.

Example 1

Synthesis of Compounds of Formula Ia

The following compounds of Formula Ia were prepared using the methods of Scheme I and Scheme Ia.

41

4-Ethoxy-2-isopropoxy-5(4-phenyl-piperzin-1-ylmethyl)-tetrahydro-furan-3-ol

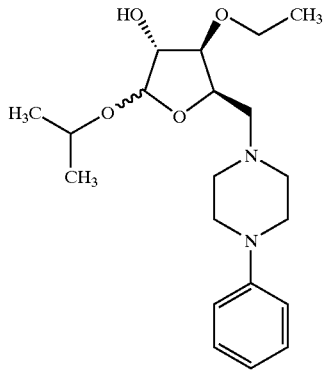

Molecular Formula: $C_{20}H_{32}N_2O_4$; Molecular Weight: 364.48

$^1$H NMR (270 MHz, CD$_3$OD) δ 7.26–7.18 (m, 2H), 6.96 (dd, J=8.7, 0.9 Hz, 2H), 6.83 (t, J=7.1 Hz, 1H), 5.08 (d, J=4.5 Hz, 1H), 4.43 (ddd, J=8.7, 5.9, 3.2 Hz, 1H), 4.01 (t, J=4.2 Hz, 1H), 3.95 (t, J=6.2 Hz, 1H), 3.90–3.85 (m, 1H), 3.77–3.66 (m, 1H), 3.58–3.47 (m, 1H), 3.18 (t, J=5.2 Hz, 4H), 2.82–2.63 (m, 5H), 2.55 (dd, J=13.6, 8.2 Hz, 1H), 1.25–1.17 (m, 9H); $^{13}$C NMR (67.5 MHz, CD$_3$OD) δ 146.9, 124.3, 115.4, 111.7, 95.3, 80.0, 72.2, 70.7, 66.0, 61.1, 53.4, 49.0, 44.5, 18.1, 16.4, 9.9; MS (ESI) m/z 365.7 [(M+H)$^+$]; Anal. Calcd for $C_{20}H_{32}N_2O_4$: C, 65.91; H, 8.85; N, 7.69; Found: C, 65.88; H, 8.73; N, 7.62.

5-[(Benzyl-phenethyl-amino)-methyl]-4-ethoxy-2-(2-methoxy-ethoxy)-tetrahydro-furan-3-ol

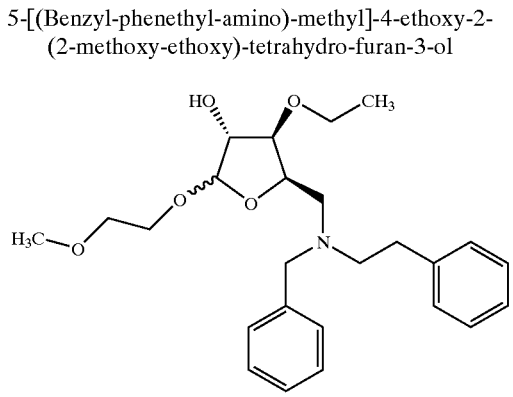

Molecular Formula: $C_{25}H_{35}NO_5$; Molecular Weight: 429.55

$^1$H NMR (270 MHz, CD$_3$OD) δ 7.34–7.19 (m, 7H), 7.15–7.10 (m, 3H), 4.99 (d, J=4.5 Hz, 1H), 4.39–4.34 (m, 1H), 4.03 (dd, J=4.2, 3.9 Hz, 1H), 3.87–3.75 (m, 3H), 3.68–3.47 (m, 6H), 3.35 (s, 3H), 3.31 (s, 1H), 3.01–2.62 (m, 6H), 1.13–1.06 (m, 3H); $^{13}$C NMR (67.5 MHz, CD$_3$OD) δ 141.9, 140.5, 130.3, 129.8, 129.3, 129.2, 128.0, 126.9, 110.3, 102.7, 85.7, 81.1, 79.8, 78.1, 72.9, 68.5, 68.1, 66.7, 60.0, 59.1, 57.4, 54.0, 34.0, 15.6; MS (ESI) m/z 430.5 [(M+H)$^+$]; Anal. Calcd for $C_{25}H_{35}NO_5$: C, 69.90; H, 8.21; N, 3.26; Found: C, 69.73; H, 8.23; N, 3.21.

42

4-Ethoxy-2-methoxy-5-(1,3,4,5-tetrahydro-pyrido[4,3-b]indol-2-ylmethyl)-tetrahydro-3-ol

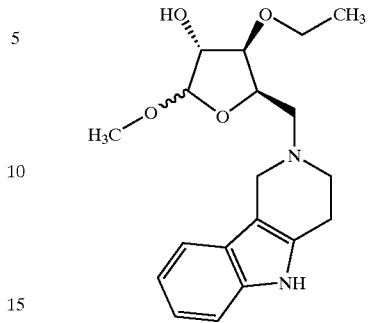

Molecular Formula: $C_{19}H_{26}N_2O_4$; Molecular Weight: 346.42

$^1$H NMR (270 MHz, CD$_2$Cl$_2$) δ 7.89 (bs, 1H), 7.42 (dd, J=6.7, 0.7 Hz, 1H), 7.35 (dt, J=8.4, 0.7 Hz, 1H), 7.11–7.00 (m, 2H), 4.95 (d, J=4.7 Hz, 1H), 4.38 (ddd, J=7.4, 4.7, 4.7 Hz, 1H), 4.10 (dd, J=1.5, 3.0 Hz, 1H), 3.83–3.62 (m, 4H), 3.54–3.45 (m, 4H), 2.96–2.85 (m, 3H), 2.78–2.69 (m, 3H), 1.18 (t, J=7.0 Hz, 3H); $^{13}$C NMR (67.5 MHz, CD$_2$Cl$_2$) δ 136.4, 132.7, 127.6, 121.4, 119.5, 118.1, 111.0, 108.5, 102.4, 85.3, 77.5, 76.8, 65.9, 57.0, 56.0, 52.0, 51.1, 21.7, 15.5; MS (ESI) m/z 347.4 [(M+H)$^+$]; Anal. Calcd for $C_{19}H_{26}N_2O_4$: C, 65.87; H, 7.56; N, 8.09; Found: C, 65.63; H, 7.39; N, 7.90.

5-[4-(3-Chloro-phenyl)-piperazin-1-ylmethyl]-2-cyclopropylmethoxy-4-ethoxy-tetrahydro-furan-3-ol

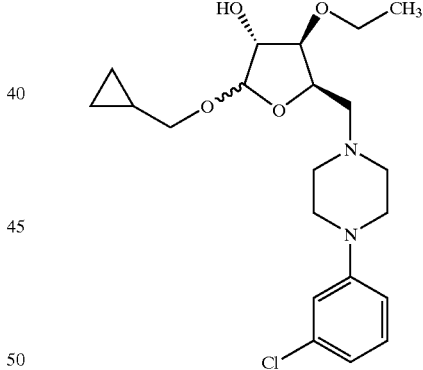

Molecular Formula: $C_{21}H_{31}ClN_2O_4$; Molecular Weight: 410.93

$_1$H NMR (270 MHz, CD$_3$OD) δ 7.17 (t, J=8.4 Hz, 1H), 6.93–6.84 (m, 2H), 6.79–6.76 (m, 1H), 4.88 (m, 1H), 4.42 (ddd, J=8.4, 5.7, 3.2 Hz, 1H), 4.05 (dd, J=4.5, 2.7 Hz, 1H), 3.75 (q, J=2.7 Hz, 1H), 3.70–3.61 (m, 2H), 3.59–3.47 (m, 2H), 3.20 (t, J=5.2 Hz, 4H), 2.86–2.58 (m, 6H), 1.19 (t, J=6.9 Hz, 3H), 1.08–1.02 (m, 1H), 0.54–0.49 (m, 2H), 0.24–0.19 (m, 2H); $^{13}$C NMR (67.5 MHz, CD$_3$OD) δ 154.0, 135.9, 131.2, 120.2, 116.7, 115.2, 109.8, 86.0, 80.2, 80.0, 73.7, 66.7, 59.5, 54.8, 15.6, 11.3, 3.8, 3.2; MS (ESI) m/z 411.8 [(M+H)$^+$]; Anal. Calcd for $C_{21}H_{31}ClN_2O_4$: C, 61.38; H, 7.60; N, 6.82; Found: C, 61.35; H, 7.63; N, 6.78.

5-Dialkylaminomethyl-2-isobutoxy-4-(naphthalen-2-ylmethoxy)tetrahydro-furan-3-ol

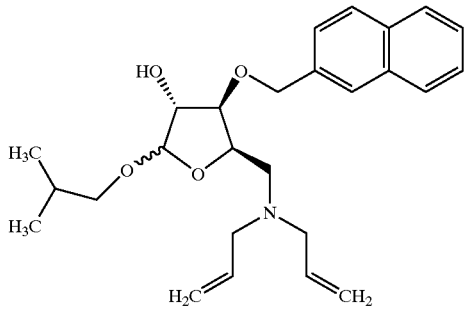

Molecular Formula: C$_{26}$H$_{35}$NO$_4$; Molecular Weight: 425.56

$^1$H NMR (270 MHz, CD$_2$Cl$_2$) δ 7.84–7.79 (m, 4H), 7.51–7.42 (m, 3H), 5.92–5.78 (m, 2H), 5.17–5.04 (m, 4H), 4.81 (d, J=2.0 Hz, 1H), 4.73 (q, J=12.4 Hz, 2H), 4.34 (ddd, J=7.4, 5.7, 4.5 Hz, 1H), 4.21 (dd, J=2.7, 2.0 Hz, 1H), 3.89 (q, J=3.0 Hz, 1H), 3.50 (dd, J=6.9, 9.3 Hz, 1H), 3.26–3.04 (m, 5H), 2.93 (dd, J=13.8, 4.2 Hz, 1H), 2.67 (dd, J=13.9, 7.5 Hz, 1H), 1.88–1.80 (m, 1H), 0.90 (d, J=6.7 Hz, 6H); $^{13}$C NMR (67.5 MHz, CD$_2$Cl$_2$) δ 136.1, 135.8, 133.3, 133.0, 128.0, 127.8, 127.6, 126.2, 125.9, 125.7, 116.9, 108.6, 84.0, 79.8, 79.3, 75.1, 72.1, 57.4, 28.6, 19.2; MS (ESI) m/z 426.5 [(M+H)$^+$]; Anal. Calcd for C$_{26}$H$_{35}$NO$_4$: C, 73.38; H, 8.29; N, 3.29; Found: C, 73.10; H, 8.32; N, 3.21.

2-(3-Methoxy-3-methyl-butoxy)-5-morpholin-4-ylmethyl-4-(naphthalen-2-yl methoxy)-tetrahydro-3-furan-3-ol

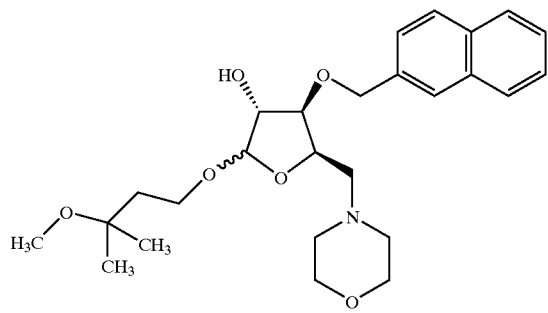

Molecular Formula: C$_{26}$H$_{37}$NO$_6$; Molecular Weight: 459.58

$^1$H NMR (270 MHz, CD$_3$OD) δ 7.85–7.82 (m, 4H), 7.50–7.43 (m, 3H), 4.85–4.80 (m, 2H), 4.66 (d, J=12.1 Hz, 1H), 4.43 (ddd, J=8.7, 5.5, 3.5 Hz, 1H), 4.18 (t, J=1.7 Hz, 1H), 3.92 (dd, J=5.3, 2.0 Hz, 1H), 3.83 (ddd, J=9.7, 7.2, 7.2 Hz, 1H), 3.66 (t, J=4.7 Hz, 4H), 3.48 (ddd, J=9.6, 7.2, 7.2 Hz, 1H), 3.16 (s, 3H), 2.81 (dd, J=13.6, 3.5 Hz, 1H), 2.69–2.57 (m, 3H), 2.51–2.43 (m, 2H), 1.82 (t, J=7.2 Hz, 2H), 1.16 (s, 3H), 1.15 (s, 3H); $^{13}$C NMR (67.5 MHz, CD$_3$OD) δ 135.7, 133.2, 127.7, 127.5, 127.4, 126.2, 125.8, 125.6, 109.0, 84.1, 78.9, 78.2, 74.1, 71.7, 66.4, 64.2, 58.8, 54.0, 38.9, 24.4, 24.3; MS (ESI) m/z 460.5 [(M+H)$^+$]; Anal. Calcd for C$_{26}$H$_{37}$NO$_6$: C, 67.95; H, 8.11; N, 3.05; Found: C, 67.92; H, 8.02; N, 3.00.

5-[(Benzyl-methyl-amino)-methyl]-4-(naphthalen-2-yl methoxy)-2-pent-2-ynyloxy-tetrahydro-furan-3-ol

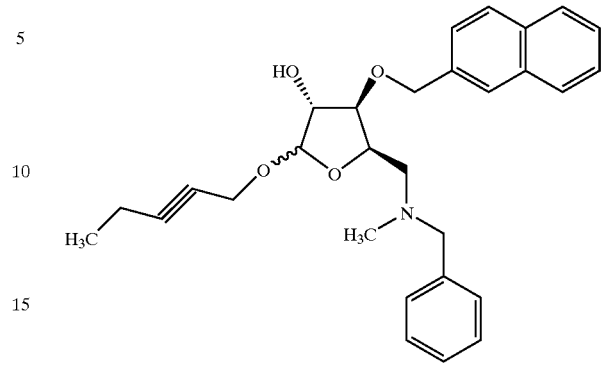

Molecular Formula: C$_{29}$H$_{33}$NO$_4$; Molecular Weight: 459.58

$^1$H NMR (270 MHz, CD$_3$OD) δ 7.84–7.74 (m, 4H), 7.49–7.37 (m, 3H), 7.30–7.19 (m, 5H), 5.20 (d, J=4.4 Hz, 1H), 4.84–4.76 (m, 1H), 4.62 (d, J=12.1 Hz, 1H), 4.44–4.37 (m, 1H), 4.30 (t, J=2.3 Hz, 1H), 4.23–4.17 (m, 2H), 4.04 (dd, J=5.8, 4.2 Hz, 1H), 3.64–3.48 (m, 2H), 2.82 (dd, J=3.5, 13.8 Hz, 1H), 2.71–2.55 (m, 1H), 2.27–2.15 (m, 2H), 2.25 (s, 3H), 1.14–1.06 (m, 3H); $^{13}$C NMR (67.5 MHz, CDCl$_3$) δ 137.8, 135.6, 133.4, 129.3, 127.9, 127.8, 127.6, 127.4, 127.0, 126.2, 125.8, 125.6, 125.5, 99.1, 83.9, 77.0, 76.0, 71.8, 62.1, 56.1, 54.7, 41.8, 12.9, 11.7; MS (ESI) m/z 460.4 [(M+H)$^+$]; Anal. Calcd for C$_{29}$H$_{33}$NO$_4$: C, 75.79; H, 7.24; N, 3.05; Found: C, 75.75; H, 7.30; N, 2.99.

4-Methoxy-5-(4-phenyl-piperazin-1-ylmethyl)-2-propoxy-tetrahydro-furan-3-ol

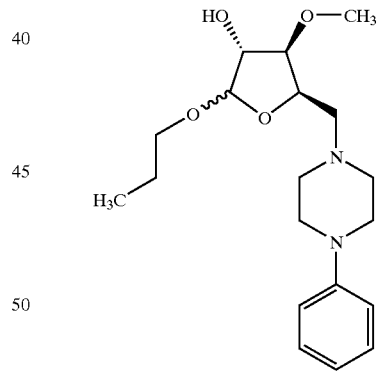

Molecular Formula: C$_{19}$H$_{30}$N$_2$O$_4$; Molecular Weight: 350.45

$^1$H NMR (270 MHz, CD$_2$Cl$_2$) δ 7.25–7.18 (m, 2H), 6.92–6.83 (m, 2H), 6.83–6.77 (m, 1H), 4.82 (d, J=2.0 Hz, 1H), 4.39 (dddd, J=7.6, 5.7, 3.7 Hz, 1H), 4.11 (dd, J=2.7, 2.0 Hz, 1H), 3.70–3.61 (m, 2H), 3.41–3.31 (m, 4H), 3.16 (t, J=4.9 Hz, 4H), 2.79–2.52 (m, 6H), 2.24 (bs, 1H), 1.63–1.51 (m, 2H), 0.89 (t, J=7.4 Hz, 3H); $^{13}$C NMR (67.5 MHz, CD$_2$Cl$_2$) δ 147.3, 124.7, 115.0, 111.5, 104.4, 82.1, 74.8, 74.7, 65.8, 53.83, 53.77, 50.0, 44.8, 18.6, 6.1; MS (ESI) m/z 351.8 [(M+H)$^+$]; Anal. Calcd for C$_{19}$H$_{30}$N$_2$O$_4$: C, 65.12; H, 8.63; N, 7.99; Found: C, 64.99; H, 8.54; N, 7.88.

2-Cyclopropylmethoxy-5-(3,4-dihydro-1H-isoquinolin-2-ylmethyl)-4-methoxy-tetrahydro-furan-3-ol

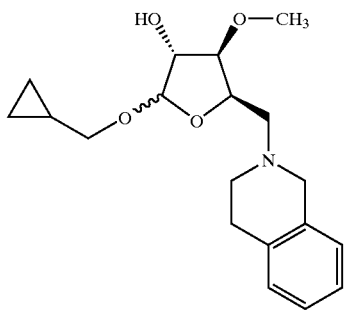

Molecular Formula: $C_{19}H_{27}NO_4$; Molecular Weight: 333.42

$^1$H NMR (270 MHz, $CD_2Cl_2$) δ 7.12–7.00 (m, 4H), 5.11 (d, J=4.7 Hz, 1H), 4.44–4.38 (m, 1H), 4.12–4.09 (m, 1H), 3.69 (s, 2H), 3.39 (s, 3H), 3.68–3.35 (m, 3H), 2.87–2.78 (m, 5H), 2.63 (dd, J=13.6, 7.7 Hz, 1H), 1.10–1.02 (m, 1H), 0.56–0.58 (m, 2H), 0.28–0.18 (m, 2H); $^{13}$C NMR (67.5 MHz, $CD_2Cl_2$) δ 135.2, 134.6, 128.9, 126.8, 126.4, 125.9, 100.8, 87.3, 77.0, 76.4, 73.5, 57.9, 57.2, 56.6, 51.7, 29.3, 10.8, 3.4, 3.0; MS (ESI) m/z 334.5 [(M+H)$^+$]; Anal. Calcd for $C_{19}H_{27}NO_4$: C, 68.44; H, 8.16; N, 4.20; Found: C, 68.19; H, 8.15; N, 4.18.

5-[(Benzyl-methyl-amino)-methyl]-4-methoxy-2-pent-2-ynyloxy-tetrahydro-furan-3-ol

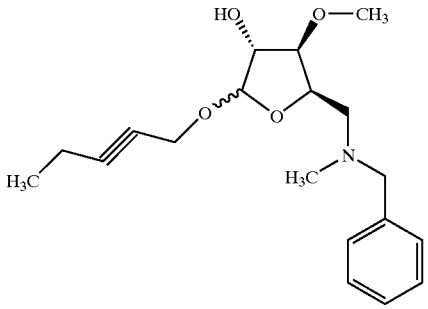

Molecular Formula: $C_{19}H_{27}NO_4$; Molecular Weight: 333.42

$^1$H NMR (270 MHz, $CD_2Cl_2$) δ 7.34–7.19 (m, 5H), 5.23 (d, J=4.7 Hz, 1H), 4.38–4.28 (m, 2H), 4.24–4.09 (m, 2H), 3.67–3.61 (m, 1H), 3.53 (d, J=9.4 Hz, 1H), 3.43 (dd, J=16.1, 3.5 Hz, 1H), 3.35 (s, 3H), 3.18 (s, 1H), 2.74 (dd, J=13.6, 4.5 Hz, 1H), 2.50 (dd, J=13.6, 7.2 Hz, 1H), 2.25–2.15 (m, 2H), 2.20 (s, 3H), 1.11 (t, J=7.4 Hz, 3H); $^{13}$C NMR (67.5 MHz, $CD_2Cl_2$) δ 139.8, 130.5, 129.3, 128.7, 128.4, 128.0, 127.2, 108.2, 99.3, 89.4, 89.1, 87.1, 85.9, 77.7, 76.5, 62.9, 57.8, 56.4, 56.0, 42.9, 13.9, 12.7; MS (ESI) m/z 334.5 [(M+H)$^+$]; Anal. Calcd for $C_{19}H_{27}NO_4$: C, 68.44; H, 8.16; N, 4.20; Found: C, 68.48; H, 8.03; N, 4.10.

4-Butoxy-2-(2-methoxy-ethoxy)-5-[(methyl-phenethyl-amino)-methyl]-tetrahydro-furan-3-ol

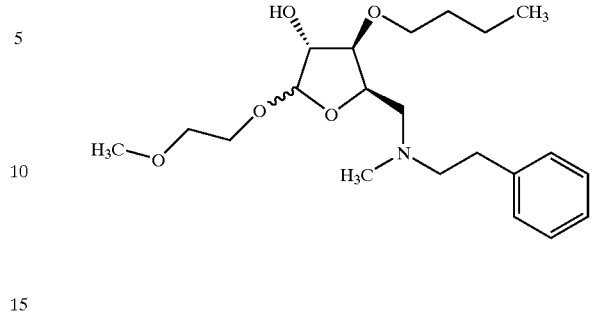

Molecular Formula: $C_{21}H_{35}NO_5$; Molecular Weight: 381.51

$^1$H NMR (270 MHz, $CD_2Cl_2$) δ 7.29–7.12 (m, 5H), 5.06 (d, J=4.7 Hz, 0.67H), 4.94 (d, J=4.2 Hz, 0.33H), 4.29–3.35 (m, 10H), 3.32 (s, 3H), 2.81–2.49 (m, 6H), 2.42 (s, 1H), 2.34 (d, J=1.8 Hz, 1H), 2.32 (s, 1H), 1.54–1.45 (m, 2H), 1.42–1.25 (m, 2H), 0.89 (t, J=7.2 Hz, 3H); $^{13}$C NMR (67.5 MHz, $CD_2Cl_2$) δ 141.3, 129.1, 128.8, 128.6, 126.4, 126.1, 110.6, 101.7, 88.2, 85.6, 85.4, 77.5, 76.9, 76.7, 72.1, 72.0, 70.2, 67.9, 67.1, 62.0, 60.3, 59.7, 59.0, 56.6, 45.0, 42.8, 34.0, 32.3, 32.2, 19.7, 19.7, 14.0; MS (ESI) m/z 382.8 [(M+H)$^+$]; Anal. Calcd for $C_{21}H_{35}NO_5$: C, 66.11; H, 9.25; N, 3.67; Found: C, 66.00; H, 9.12; N, 3.62.

4-Butoxy-2-methoxy-5-(1,3,4,5-tetrahydro-pyrido[4,3-b]indol-2-ylmethyl)-tetrahydro-furan-3-ol

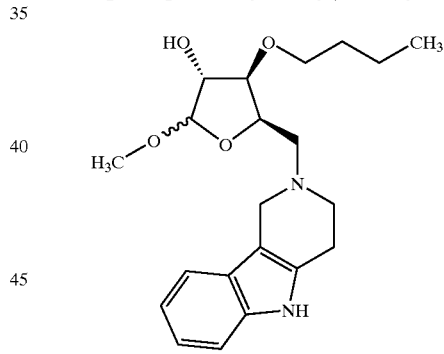

Molecular Formula: $C_{21}H_{30}N_2O_4$; Molecular Weight: 374.47

1H NMR (270 MHz, $CD_2C_2$) δ 7.95 (bs, 1H), 7.42 (dd, J=7.7, 1.0 Hz, 1H), 7.31–7.27 (m, 1H), 7.09–7.02 (m, 2H), 4.96 (d, J=4.7 Hz, 1H), 4.44–4.38 (m, 0.5H), 4.26–4.23 (m, 0.5H), 4.11–3.98 (m, 1H), 3.92 (s, 2H), 3.84–3.47 (m, 2H), 3.47 (s, 2H), 3.44–3.38 (m, 1H), 3.32 (s, 3H), 3.20–3.11 (m, 1H), 2.99–2.68 (m, 4H), 1.57–1.48 (m, 2H), 1.41–1.31 (m, 2H), 0.90 (t, J=7.2 Hz, 3H); $^{13}$C NMR (67.5 MHz, $CD_2Cl_2$) δ 131.4, 127.4, 126.6, 122.6, 116.8, 116.5, 114.6, 114.5, 113.2, 113.1, 106.8, 106.0, 103.4, 103.3, 97.4, 83.4, 80.9, 80.5, 72.4, 71.7, 71.5, 65.4, 65.2, 53.8, 51.9, 51.0, 50.2, 47.7, 46.9, 46.0, 27.3, 27.2, 16.6, 16.0, 14.7, 14.6, 9.0; MS (ESI) m/z 375.5 [(M+H)$^+$]; Anal. Calcd for $C_{21}H_{30}N_2O_4$: C, 67.35; H, 8.07; N, 7.48; Found: C, 67.09; H, 7.89; N, 7.40.

4-(3-Methoxy-benzyloxy)-2-(3-methoxy-3-methyl-butoxy)-5-morpholin-4-ylmethyl-tetrahydro-furan-3-ol

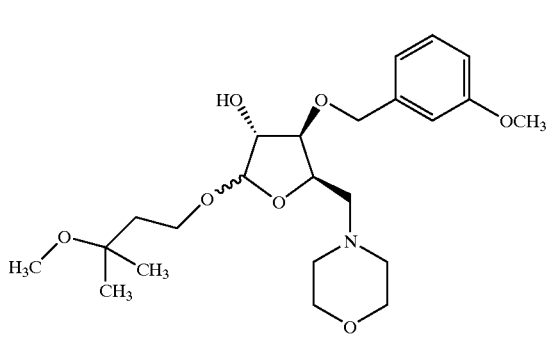

Molecular Formula: $C_{23}H_{37}NO_7$; Molecular Weight: 439.54

1H NMR (270 MHz, $CD_2Cl_2$) δ 7.24 (t, J=7.7 Hz, 1H), 6.91–6.78 (m, 3H), 5.05 (d, J=4.7 Hz, 1H), 4.67 (d, J=11.9 Hz, 1H), 4.50 (d, J=12.1, 1H), 4.34–4.28 (m, 1H), 4.18–4.14 (m, 1H), 3.80 (s, 3H), 3.67–3.62 (m, 7H), 3.12 (s, 3H), 2.71–2.41 (m, 6H), 1.81–1.75 (m, 2H),1.13 (s, 6H); $^{13}C$ NMR (67.5 MHz, $CD_2Cl_2$) δ 160.1, 140.2, 129.7, 120.1, 113.4, 113.3, 101.5, 85.0, 76.8, 76.6, 73.9, 71.9, 67.2, 65.5, 58.2, 55.5, 49.3, 39.6, 25.5, 25.3; MS (ESI) m/z 440.6 [(M+H)$^+$]; Anal. Calcd for $C_{23}H_{37}NO_7$: C, 62.85; H, 8.48; N, 3.19; Found: C, 62.65; H, 8.30; N, 3.16.

5-Diallylaminomethyl-2-isobutoxy-4-(3-methoxy-benzyloxy)-tetrahydro-furan-3-ol

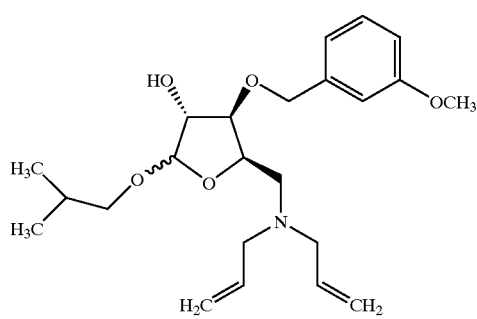

Molecular Formula: $C_{23}H_{35}NO_5$; Molecular Weight: 405.53

$^1H$ NMR (270 MHz, $CD_2Cl_2$) δ 7.26–7.19 (m, 1H), 6.90–6.78 (m, 3H), 5.89–5.71 (m, 1H), 5.89–5.71(m, 1H), 5.19–5.03 (m, 3H), 4.89 (s, 1H), 4.67–4.42 (m, 1H), 4.30–4.11 (m, 2H), 4.01 (s, 1H), 3.85–3.82 (m, 1H), 3.77 (s, 3H), 3.66–3.52 (m, 1H), 3.40–2.56 (m, 9H), 1.93–1.82 (m, 1H), 0.90 (d, J=5.7 Hz 6H), 0.86 (d, J=2.0 Hz, 1H); $^{13}C$ NMR (67.5 MHz, $CD_2Cl_2$) δ 156.3, 136.5, 136.4, 132.31, 132.25, 131.0, 125.8, 116.5, 116.3, 115.3, 113.9, 113.7, 109.6, 106.6, 97.3, 83.4, 81.3, 73.5, 71.6, 70.7, 67.9, 55.4, 54.0, 53.6, 51.7, 48.9, 25.0, 15.6; MS (ESI) m/z 406.5 [(M+H)$^+$]; Anal. Calcd for $C_{23}H_{35}NO_5$: C, 68.12; H, 8.70; N, 3.45; Found: C, 67.97; H, 8.57; N, 3.46.

5-[(Dibenzylamino)-methyl]-2-ethoxy-4-(3-methoxy-benzyloxy)-tetrahydro-furan-3-ol

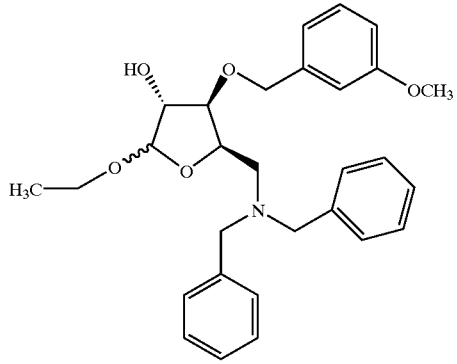

Molecular Formula: $C_{29}H_{35}NO_5$; Molecular Weight: 477.59

$^1H$ NMR (270 MHz, $CD_2Cl_2$) δ 7.39–7.15 (m, 11H), 6.79–6.70 (m, 3H), 4.81 (d, J=2.2 Hz, 1H), 4.41 (d, J=12.1 Hz, 1H), 4.27 (d, J=12.1 Hz, 1H), 4.10 (bs, 1H), 3.83–3.64 (m, 6H), 3.73 (s, 3H), 3.56–3.37 (m, 2H), 2.94 (dd, J=14.1, 3.2 Hz, 1H), 2.72 (dd, J=14.1, 7.9 Hz, 1H), 1.55 (bs, 1H), 1.14 (t, J=6.9 Hz, 3H); 13C NMR (67.5 MHz, $CD_2Cl_2$) δ 129.6, 129.2, 128.5, 127.1, 120.1, 113.5, 113.4, 108.6, 84.2, 79.8, 72.0, 64.3, 59.1, 55.5, 15.3; MS (ESI) m/z 478.7 [(M+H)$^+$]; Anal. Calcd for $C_{29}H_{35}NO_5$: C, 72.93; H, 7.39; N, 2.93; Found: C, 72.77; H, 7.39; N, 2.95.

Example 2

The following compounds of Formula Ib were prepared using the methods of Scheme I and Scheme Ib.

Cyclohexanecarboxylic acid (6-benzyloxy-2.2-dimethyl-tetrahydro-furo[2,3-d][1,3]dioxol-5-ylmethyl)-(2-diethylamino-ethyl)-amide

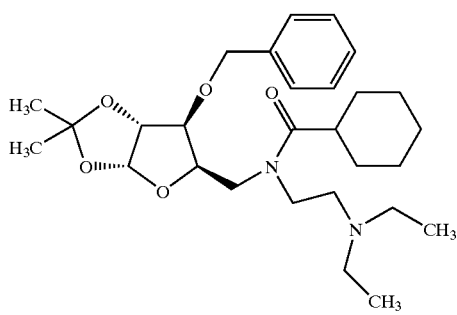

Molecular Formula: $C_{28}H_{44}N_2O_5$; Molecular Weight: 488.7

$^1H$ NMR (270 MHz, $CDCl_3$) δ 7.27 (m, 5H), 5.86 (t, 1H), 4.70–4.40 (m, 3H), 4.29–4.09 (m, 2H), 3.89 (d, J=3.2Hz, 1H, major rotamer), 3.82 (d, J=3.2Hz, 1H, minor rotamer), 3.71 (d, J=7.4 Hz, 1H, minor rotamer), 3.65 (d, J=7.7 Hz, 1H, major rotamer), 3.57–3.20 (m, 3H), 3.05 (dd, J=14.3, 8.2 Hz, 1H), 2.60–2.37 (m, 7H), 1.80–1.45 (m, 6H), 1.40 (s, 3H), (s, 3H, minor rotamer), 1.37 (s, 3H, major rotamer), 1.25 (s, 3H, minor rotamer), 1.23 (s, 3H, major rotamer), 1.19–1.02 (m, 2H), 0.96 (m, 6H); $^{13}C$ NMR (67.5 MHz, $CDCl_3$) δ 176.6, 176.4, 137.2, 136.9, 128.2, 127.4, 127.3, 111.4, 111.3, 104.9, 104.6, 81.7, 79.9, 71.8, 71.3, 51.9, 47.4, 47.3, 47.2. 46.2, 40.4, 40.2, 29.3, 25.7, 25.6, 25.5, 11.8, 11.6; MS (ESI) m/z 489.3 [(M+H)+]; Anal. Calcd for $C_{28}H_{44}N_2O_5$ (488.7): C, 68.82; H, 9.08; N, 5.73; Found: C, 68.80; H, 8.83; N, 5.63.

N-(6-Benzyloxy-2,2-dimethyl-tetrahydro-furo[2,3-d][1,3]dioxol-5-ylmethyl)-N-(2-methoxy-benzyl)-2,2-diphenyl-acetamide

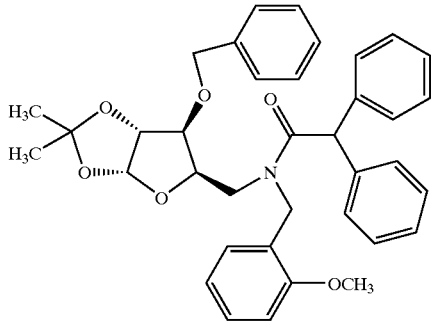

Molecular Formula: $C_{37}H_{39}NO_6$; Molecular Weight: 593.71

$^1$H NMR (270 MHz, $CDCl_3$) δ 7.36–7.25 (m, 10 H), 7.14–7.10 (m, 5H), 7.04–6.81 (m, 4H), 6.06 (d, J=3.9 Hz, 2H, minor rotamer), 5.94 (d, J=3.7 Hz, 2H, major rotamer), 5.56 (s, 1H, minor rotamer), 5.09 (s, 1H, major rotamer), 4.79–4.12 (m, 5H), 3.89 (d, J=3.2 Hz, 1H), 3.71 (s, 3H, major rotamer), 3.60 (s, 3H, minor rotamer), 3.22–3.12 (m, 2H), 1.44 (s, 3H, major rotamer), 1.36 (s, 3H, minor rotamer), 1.26 (s, 3H, minor rotamer), 1.25 (s, 3H, major rotamer); $^{13}$C NMR (67.5 MHz, $CDCl_3$) δ 172.7, 172.4, 157.3, 156.9, 140.5, 140.0, 137.1, 136.9, 129.3, 128.9, 128.6, 128.4, 128.3, 128.0, 127.8, 127.5, 127.5, 126.9, 126.8, 126.7, 125.4, 120.5, 111.6, 111.5, 104.9, 104.7, 82.5, 81.9, 81.8, 79.5, 78.3, 71.8, 71.4, 55.0, 54.0, 48.3, 46.6, 46.2, 44.0, 26.8, 26.6, 26.4, 26.1; MS (ESI) m/z 594.3 [(M+H)+]; Anal. Calcd for $C_{37}H_{39}NO_6$ (593.71): C, 74.85; H, 6.62; N, 2.36; Found: C, 74.68; H, 6.56; N, 2.26.

N-Butyl-N-[6-(3-methoxy-benzyloxy)-2,2-dimethyl-tetrahydro-furo[2,3-d][1,3]dioxol-5-ylmethyl]-benzamide

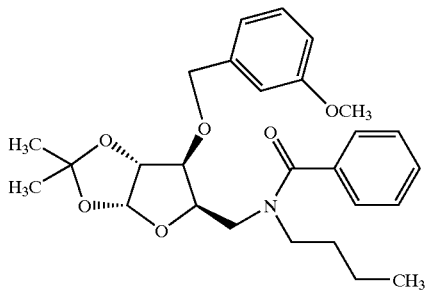

Molecular Formula: $C_{27}H_{35}NO_6$; Molecular Weight: 469.57

$^1$H NMR (270 MHz, $CDCl_3$) δ 7.35 (s, 7H), 6.95–6.81 (m, 2H), 5.94 (s, 1H), 4.69–4.50 (m, 5H), 4.29–4.05 (m, 3H), 3.77 (s, 3H), 3.41–3.33 (m, 2H), 1.53 (s, 3H), 1.30 (s, 3H), 1.23 (t, 3H), 0.76–0.74 (m, 3H); $^{13}$C NMR (67.5 MHz, $CDCl_3$) δ 172.6, 171.8, 170.7, 159.4, 138.7, 138.3, 136.5, 129.5, 128.9, 127.9, 126.3, 119.6, 113.0, 112.9, 111.3, 104.8, 82.5, 81.7, 79.2, 71.5, 71.0, 60.0, 54.8, 49.8, 45.2, 44.2, 30.3, 26.5, 25.9, 20.6, 20.4, 19.8, 19.3, 13.9, 13.3; MS (ESI) m/z 470.2 [(M+H)+]; Anal. Calcd for $C_{27}H_{35}NO_6$ (469.57): C, 69.06; H, 7.51; N, 2.98; Found: C, 69.12; H, 7.52; N, 2.86.

N-(2,4-Dimethoxy-benzyl)-N-(6-methoxy-2,2-dimethyl-tetrahydro-furo[2,3-d][1,3]dioxol-5-ylmethyl)-2,2-diphenyl-acetamide

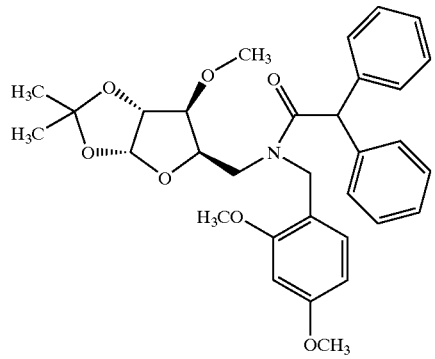

Molecular Formula: $C_{32}H_{37}NO_7$; Molecular Weight: 547.6

$^1$H NMR (270 MHz, $CDCl_3$) δ 7.32–7.11 (m, 10H), 7.04 (d, J=8.9 Hz, 1H), 6.47 (s, 1H, major rotamer), 6.44 (s, 1H, minor rotamer), 6.41–6.36 (m, 1H), 5.95 (d, J=4.0 Hz, 1H, minor rotamer), 5.86 (d, J=4.0 Hz, 1H, major rotamer), 5.63 (s, 1H, minor rotamer), 5.00 (s, 1H, major rotamer), 4.82–4.40 (m, 3H), 4.29 (ddd, J=7.2, 3.7, 3.7 Hz, 1H), 4.14 (dd, J=14.3, 2.6 Hz, 1H), 3.76 (s, 3H), 3.74 (s, 3H), 3.46 (d, J=3.2 Hz, 1H), 3.28 (s, 3H), 3.19 (dd, J=14.3, 8.5 Hz, 1H), 1.51 (s, 3H), 1.31 (s, 3H); $^{13}$C NMR (67.5 MHz, $CDCl_3$) δ 172.5, 172.2, 160.2, 160.0, 158.2, 157.9, 140.3, 139.9, 139.1, 130.5, 129.1, 128.8, 128.4, 128.3, 127.9, 127.8, 126.8, 126.6, 126.5, 126.3, 117.7, 117.4, 111.3, 111.2, 104.8, 104.5, 103.9, 103.7, 98.4, 98.0, 84.6, 84.0, 81.0, 80.9, 79.2, 78.3, 57.4, 57.2, 55.1, 55.0, 54.9, 53.9, 53.6, 47.7, 45.9, 45.4, 43.4, 34.4, 31.3, 26.6, 26.4, 26.2, 22.4; MS (ESI) m/z 548.5 [(M+H)+]; Anal. Calcd for $C_{32}H_{37}NO_7$ (547.6): C, 70.18; H, 6.81; N, 2.56; Found: C, 69.92; H, 6.67; N, 2.48.

Cyclohexanecarboxylic acid (6-benzyloxy-2,2-dimethyl-tetrahydro-furo[2,3-d][1,3]dioxol-5-ylmethyl)-(3-methoxy-propyl)-amide

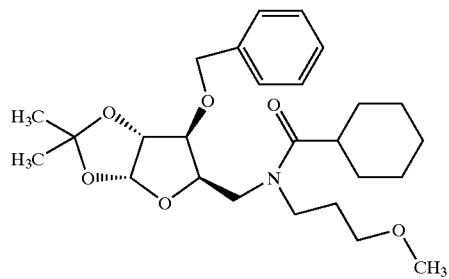

Molecular Formula: $C_{26}H_{39}NO_6$; Molecular Weight: 461.6

$^1$H NMR (270 MHz, $CDCl_3$) δ 7.37–7.24 (m, 5H), 5.90 (d, J=3.9 Hz, 1H), 4.75–4.43 (m, 3H), 4.35 (ddd, J=7.9, 2.7, 2.7 Hz, 1H), 4.15 (dd, J=14.3, 2.5 Hz, 1H), 3.96 (d, J=3.2 Hz, 1H, major rotamer), 3.88 (d, J=3.2 Hz, 1H, minor rotamer), 3.71 (dd, J=15.3, 7.2 Hz, 1H), 3.58–3.48 (m, 2H), 3.30 (s, 3H, major rotamer), 3.27 (s, 3H, minor rotamer), 3.35–3.26 (m, 3H), 3.07 (dd, J=14.3, 8.2 Hz, 1H), 2.60–2.48 (m, 1H), 1.86–1.54 (m, 10H), 1.42 (s, 3H, minor rotamer), 1.40 (s, 3H, major rotamer), 1.31 (s, 3H, minor rotamer), 1.29 (s, 3H, major rotamer); $^{13}$C NMR (67.5 MHz, CDCl$_3$) δ 6 176.6, 176.4, 137.1, 136.8, 128.3, 128.2, 127.9, 127.7, 127.44, 127.36, 126.6, 111.4, 111.3, 104.8, 104.6, 82.6, 81.7, 81.5, 79.7, 78.9, 71.7, 71.3, 70.0, 68.9, 58.3, 58.2, 46.1, 45.4, 43.5, 40.2, 40.0, 29.5, 29.3, 29.1, 27.5, 26.5, 26.4, 26.1, 26.0, 25.6, 25.5, 25.4; MS (ESI) m/z 463.4 [(M+H)$^+$]; Anal. Calcd for C$_{26}$H$_{39}$NO$_6$ (461.6): C, 67.65; H, 8.52; N, 3.03; Found: C, 67.73; H, 8.49; N, 2.96.

N-(1-Benzyl-pyrrolidin-3-yl)-N-[6-(3-methoxy-benzyloxy)-2,2-dimethyl-tetrahydro-furo[2,3-d][1,3]dioxol-5-ylmethyl]-benzamide

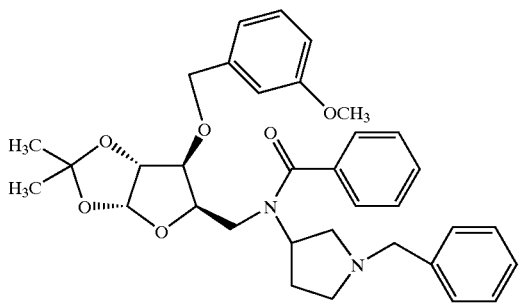

Molecular Formula: C$_{34}$H$_{40}$N$_2$O$_6$; Molecular Weight: 572.7

$^1$H NMR (270 MHz, CDCl$_3$) □7.35 (d, J=1.9 Hz, 2H), 7.31–7.19 (m, 7H), 6.93 (bs, 3H), 6.84 (dd, J=8.2, 1.9 Hz, 2H), 5.96 (d, J=3.2 Hz, 1H, minor rotamer), 5.77 (d, J=3.7 Hz, 1H, major rotamer), 4.73–4.39 (m, 4H), 4.14–4.03 (m, 3H), 3.76 (d, J=1.9 Hz, 3H), 3.65 (d, J=13.0 Hz, 1H), 3.39 (t, J=13.2 Hz, 1H), 3.22 (d, J=7.2 Hz, 1H), 2.87–2.04 (m, 5H), 1.44 (s, 3H), 1.29 (s, 3H), 1.23 (t, J=7.2 Hz, 1H); $^{13}$C NMR (67.5 MHz, CDCl$_3$) □172.1, 172.0, 159.6, 139.1, 138.7, 138.6, 136.9, 136.7, 128.3, 127.9, 126.7, 119.6, 119.5, 113.1, 113.0, 112.9, 111.3, 104.6, 104.5, 82.7, 82.2, 78.4, 78.0, 71.6, 60.1, 60.0, 59.9, 57.9, 57.1, 54.9, 53.5, 53.3, 42.5, 30.5, 29.3, 26.7, 26.6, 26.2, 26.1; MS (ESI) m/z 574.7 [(M+H)$^+$]; Anal. Calcd for C$_{34}$H$_{40}$N$_2$O$_6$ (572.7): C, 71.31; H, 7.04; N, 4.89; Found: C, 71.04; H, 7.08; N, 4.74.

Example 3

The following compounds of Formula Ic were prepared using the methods of Scheme I and Scheme Ic.

1-Benzyl-3-ethyl-1-(6-methoxy-2,2-dimethyl-tetrahydro-furo[2,3-d][1,3]dioxol-5-ylmethyl)-urea

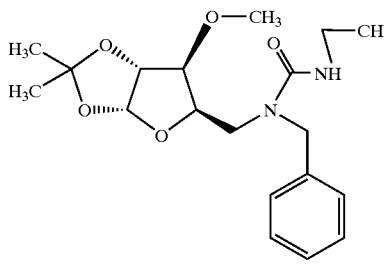

Molecular Formula: C$_{19}$H$_{28}$N$_2$O$_5$; Molecular Weight: 364.4

$^1$H NMR (270 MHz, CDCl$_3$) δ 7.34–7.20 (m, 5H), 5.87 (d, J=3.7 Hz, 1H), 5.32 (bs, 1H), 4.60–4.57 (s, 2H), 4.55 (s, 1H), 4.17 (ddd, J=7.2, 3.9, 3.9 Hz, 1H), 3.61–3.52 (m, 2H), 3.44 (d, J=7.2 Hz, 1H), 3.35 (s, 3H), 3.31–3.19 (m, 2H), 1.41 (s, 3H), 1.30 (s, 3H), 1.10 (t, J=7.2 Hz, 3H); $^{13}$C NMR (67.5 MHz, CDCl$_3$) δ 158.6, 138.2, 128.3, 127.1, 126.9, 111.4, 104.4, 83.9, 80.6, 79.1, 57.0, 50.8, 46.1, 35.4, 26.3, 25.9, 15.2; MS (ESI) m/z 365.1 [(M+H)$^+$]; Anal. Calcd for C$_{19}$H$_{28}$N$_2$O$_5$ (364.4): C, 62.62; H, 7.74; N, 7.69; Found: C, 62.39; H, 7.58; N, 7.95.

1-(6-Methoxy-2,2-dimethyl-tetrahydro-furo[2,3-d][1,3]dioxol-5-ylmethyl)-3-phenyl-1-(4-trifluoromethoxy-benzyl)-urea

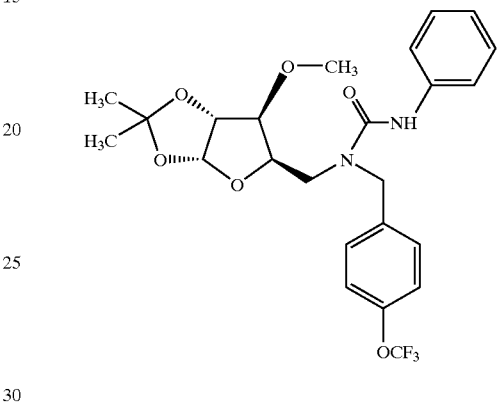

Molecular Formula: C$_{24}$H$_{27}$F$_3$N$_2$O$_6$; Molecular Weight: 496.48

$^1$H NMR (270 MHz, CDCl$_3$) δ 7.81 (s, 1H), 7.40–7.36 (m, 5H), 7.31–7.18 (m, 2H), 7.05–6.96 (m, 2H), 6.00 (d, J=3.7 Hz, 2H), 4.73–4.58 (m, 2H), 4.26–4.20 (m, 1H), 3.77–3.68 (m, 1H), 3.63–3.41 (m, 2H), 3.40 (s, 3H), 1.42 (s, 3H), 1.34 (s, 3H); $^{13}$C NMR (67.5 MHz, CDCl$_3$) δ 156.4, 148.4, 139.4, 136.9, 129.0, 128.7, 122.6, 121.1, 119.6, 119.5, 112.1, 104.8, 84.2, 80.9, 79.2, 57.5, 50.5, 47.2, 26.5, 26.1; MS (ESI) m/z 497.2 [(M+H)$^+$]; Anal. Calcd for C$_{24}$H$_{27}$F$_3$N$_2$O$_6$ (497.48): C, 58.06; H, 5.48; N, 5.64; Found: C, 58.06; H, 5.45; N, 5.51.

1-Cyclopropylmethyl-3-isopropyl-1-[6-(3-methoxy-benzyloxy)-2,2-dimethyl-tetrahydro-furo[2,3-d][1,3]dioxol-5-ylmethyl]-urea

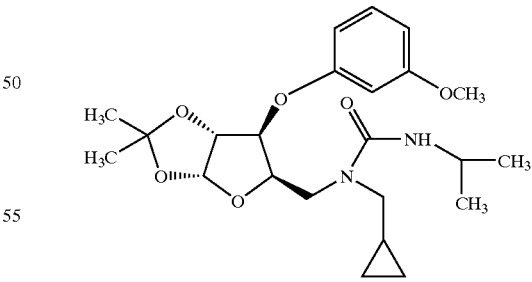

Molecular Formula: C$_{24}$H$_{36}$N$_2$O$_6$; Molecular Weight: 448.6

$^1$H NMR (270 MHz, CDCl$_3$) δ 7.36–7.30 (m, 1H), 6.97–6.89 (m, 3H), 5.89 (d, J=3.9 Hz, 1H), 5.09 (d, J=6.7 Hz, 1H), 4.64 (d, J=12.1 Hz, 1H), 4.58 (d, J=3.9 Hz, 1H), 4.41 (d, J=12.1 Hz, 1H), 4.30 (ddd, J=6.7, 3.2, 3.2 Hz, 1H), 3.92–3.75 (m, 1H), 3.75 (s, 3H), 3.59–3.48 (m, 2H), 3.45 (d, J=6.9 Hz, 1H), 3.40 (d, J=6.9 Hz, 1H), 3.23 (dd, J=14.8, 6.4

Hz, 1H), 3.02 (dd, J=14.6, 6.7 Hz, 1H), 1.41 (s, 3H), 1.26 (s, 3H), 0.97 (d, J=6.4 Hz, 6H), 0.42–0.39 (m, 2H), 0.12–0.08 (m, 2H); $^{13}$C NMR (67.5 MHz, CDCl$_3$) δ 173.3, 159.6, 158.0, 138.5, 129.4, 119.7, 113.2, 111.5, 104.7, 82.1, 81.6, 80.4, 71.3, 65.6, 54.9, 51.8, 46.9, 42.3, 26.5, 25.9, 23.3, 22.9, 20.7, 15.0, 9.9, 3.6, 3.3; MS (ESI) m/z 449.2 [(M+H)$^+$]; Anal. Calcd for C$_{24}$H$_{36}$N$_2$O$_6$ (448.6): C, 64.26; H, 8.09; N, 6.25; Found: C, 64.08; H, 8.07; N, 6.30.

3-Ethyl-1-(6-methoxy-2,2-dimethyl-tetrahydro-furo[2,3-d][1,3]dioxol-5-ylmethyl)-1-phenethyl-urea

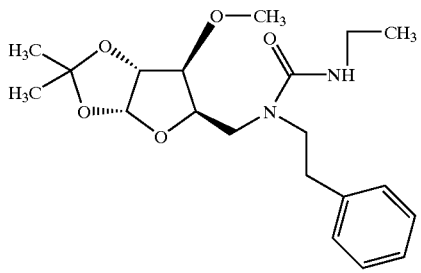

Molecular Formula: C$_{20}$H$_{30}$N$_2$O$_5$; Molecular Weight: 378.5

$^1$H NMR (270 MHz, CDCl$_3$) δ 7.32–7.15 (m, 5H), 5.88 (d, J=3.9 Hz, 1H), 5.02 (s, 1H), 4.58 (d, J=3.9 Hz, 1H), 4.26–4.21 (m, 1H), 3.61 (d, J=3.2 Hz, 1H), 3.56–3.43 (m, 3H), 3.38 (s, 3H), 3.27 (dd, J=10.7, 6.9 Hz, 1H), 3.21–3.12 (m, 2H), 2.87 (t, J=7.4 Hz, 2H), 1.46 (s, 3H), 1.33 (s, 3H), 1.06 (t, J=7.2 Hz, 3H); $^{13}$C NMR (67.5 MHz, CDCl$_3$) δ 158.1, 139.2, 128.5, 128.2, 125.9, 111.3, 104.4, 83.8, 80.6, 79.2, 57.0, 49.9, 46.2, 35.2, 34.3, 26.3, 25.8, 15.1; MS (ESI) m/z 379.1 [+H)$^+$]; Anal. Calcd for C$_{20}$H$_{30}$N$_2$O$_5$ (378.5): C, 63.47; H, 7.99; N, 7.40; Found: C, 63.22; H, 8.03; N, 7.32.

1-(6-Benzyloxy-2,2-dimethyl-tetrahydro-furo[2,3-d][1,3]dioxol-5-ylmethyl)-3-ethyl-1-[2-(1H-indol-2-yl)-ethyl]-urea

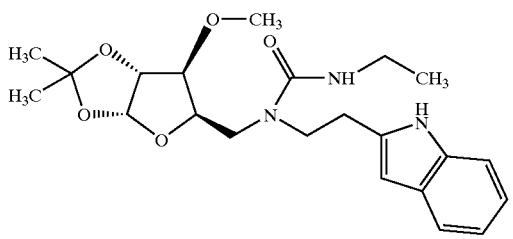

Molecular Formula: C$_{28}$H$_{35}$N$_3$O$_5$; Molecular Weight: 493.6

$^1$H NMR (270 MHz, CDCl$_3$) δ 9.11 (s, 1H), 7.58 (d, J=7.6Hz, 1H), 7.37–7.22 (m, 6H), 7.16–7.03 (m, 2H), 6.92 (d, J=1.9 Hz, 1H), 5.93 (d, J=3.7 Hz, 1H), 4.79 (bs, 1H), 4.59 (d, J=7.4 Hz, 1H), 4.56 (s, 1H), 4.34 (d, J=11.8 Hz, 2H), 3.77 (d, J=3.2 Hz, 1H), 3.71–3.60 (m, 2H), 3.44 (m, 2H), 3.14–2.90 (m, 4H), 1.42 (s, 3H), 1.28 (s, 3H), 0.82 (t, J=7.2 Hz, 3H); $^{13}$C NMR (67.5 MHz, CDCl$_3$) δ 158.7, 136.9, 136.3, 128.3, 127.9, 127.5, 126.9, 122.5, 121.5, 118.9, 118.2, 112.3, 111.5, 111.3, 104.7, 82.2, 81.6, 80.1, 71.5, 60.2, 48.9, 47.1, 35.3, 26.5, 25.9, 24.1, 14.8; MS (ESI) m/z 495.0 [(M+H)$^+$]; Anal. Calcd for C$_{28}$H$_{35}$N$_3$O$_5$ (493.6): C, 68.13; H, 7.15; N, 8.51; Found: C, 68.05; H, 6.91; N, 8.39.

1-Allyl-1-[6-(3-methoxy-benzyloxy)-2,2-dimethyl-tetrahydro-furo[2,3-d][1,3]dioxol-5-ylmethyl]-3-phenyl-urea

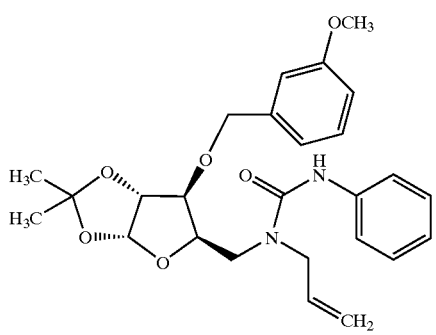

Molecular Formula: C$_{26}$H$_{32}$N$_2$O$_6$; Molecular Weight: 468.5

$^1$H NMR (270 MHz, CDCl$_3$) δ 7.49 (bs, 1H), 7.33–7.20 (m, 5H), 6.97 (ddd, J=10.2, 2.7, 1.5 Hz, 1H), 6.89–6.83 (m, 3H), 6.03 (d, J=3.9 Hz, 1H), 5.95–5.81 (m, 1H), 5.22 (d, J=1.0 Hz, 1H), 5.17 (dd, J=5.2, 1.2 Hz, 1H), 4.68 (d, J=12.3 Hz, 1H), 4.65 (s, 1H), 4.44 (d, J=12.1 Hz, 2H), 4.08 (dd, J=16.3, 5.4 Hz, 1H), 3.94 (d, J=3.2 Hz, 1H), 3.87 (d, J=5.7 Hz, 1H), 3.78 (s, 3H), 3.66–3.51 (m, 2H), 1.48 (s, 3H), 1.33 (s, 3H); $^{13}$C NMR (67.5 MHz, CDCl$_3$) δ 159.6, 156.0, 139.4, 138.4, 134.2, 129.5, 128.6, 122.3, 119.8, 119.4, 116.9, 113.4, 113.2, 111.9, 104.9, 82.0, 81.8, 80.1, 81.5, 55.0, 50.7, 47.3, 26.6, 26.1; MS (ESI) m/z 470.1 [(M+H)$^+$]; Anal. Calcd for C$_{26}$H$_{32}$N$_2$O$_6$ (468.5): C, 66.65; H, 6.88; N, 5.98; Found: C, 66.48; H, 6.69; N, 5.95.

Example 4

The following compounds of Formulas IIb and IIc were prepared using the methods of Scheme IIb and IIc, respectively. The compounds were synthesized and purified by normal phase flash chromatography using several chromatography solvents. These compounds were used to assess the purity of the corresponding compounds found in the library. Amide rotamers were present and complicated NMR analysis. Standards containing a hem acetal moiety were observed as diastereomeric mixtures. In some cases, both diastereomers and amide rotamers complicated NMR analysis. Where peaks due to diastereomers are apparent, major and minor diastereomers are noted. Diastereomers are evident in the $^1$H and $^{13}$C NMR, and all observed peaks are listed.

N-(4,5-Dihydroxy-3-methoxy-tetrahydro-furan-2-ylmethyl)-N-(2-methoxy-benzyl)-2,2-diphenyl-acetamide

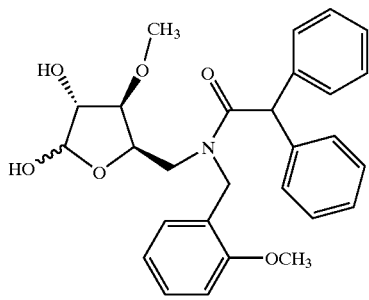

Molecular Formula: $C_{28}H_{31}NO_6$; Molecular Weight: 477.6

$^1$H NMR (270 MHz, CDCl$_3$) δ 7.20–7.10 (m, 10H), 6.90–6.70 (m, 4H), 5.57 (s, 2H), 5.21 (d, J=3.2 Hz, 1H), 5.10 (d, J=5.9 Hz, 1H), 5.00 (s, 1H), 4.51 (d, J=7.4 Hz, 1H), 4.0 (s, 1H), 3.7 (d, J=3.2 Hz, 3H), 3.44 (m, 2H), 3.19 (m, 3H); MS (ESI) m/z 478.2 [(M+H)$^+$]; Anal. Calcd for $C_{28}H_{31}NO_6$ (477.6): C, 70.42; H, 6.54; N, 2.93; Found: C, 70.24; H, 6.39; N, 2.82.

N-Butyl-N-[4,5-dihydroxy-3-(3-methoxy-benzyloxy)-tetrahydro-furan-2-ylmethyl]-benzamide

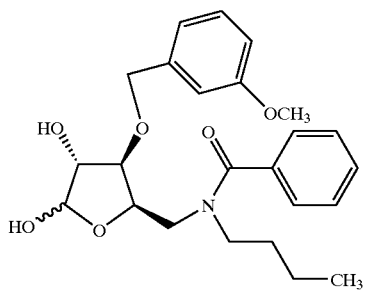

Molecular Formula: $C_{24}H_{31}NO_6$; Molecular Weight: 429.5

$^1$H NMR (270 MHz, CDCl$_3$) δ 7.35 (s, 5H), 7.30–7.23 (m, 1H), 6.90–6.82 (m, 3H), 5.35 (d, J=3.2 Hz, 2H), 5.10 (s, 1H), 4.67–4.59 (m, 1H), 4.48–4.30 (m, 1H), 4.26–3.80 (m, 1H), 3.77 (s, 3H), 3.51–3.12 (m, 4H), 1.5–1.3 (m, 2H), 1.10–1.00 (m, 2H), 0.72 (m, 3H); $^{13}$C NMR (67.5 MHz, CDCl$_3$) δ 172.6, 159.6, 139.4, 136.4, 129.6, 129.4, 128.3, 126.4, 120.1, 119.8, 113.4, 113.1, 112.9, 103.3, 96.5, 84.3, 83.3, 77.9, 77.4, 74.6, 71.6, 55.1, 45.3, 30.6, 19.5, 13.5; MS (ESI) m/z 430.4 [(M+H)$^+$]; Anal. Calcd for $C_{24}H_{31}NO_6$ (429.5): C, 67.11; H, 7.27; N, 3.26; Found: C, 66.89; H, 7.14; N, 3.20.

1-(3-Benzyloxy-4,5-dihydroxy-tetrahydro-furan-2-ylmethyl)-3-phenyl-1-(4-trifluoromethoxy-benzyl)-urea

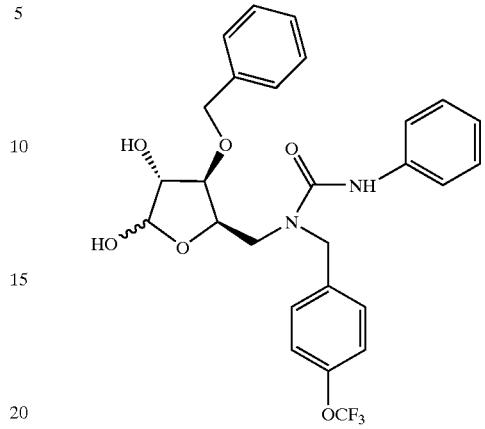

Molecular Formula: $C_{27}H_{27}F_3N_2O_6$; Molecular Weight: 532.5

$^1$H NMR (270 MHz, CDCl$_3$) δ 8.18 (s, 1H), 7.57–7.28 (m, 10H), 7.06–7.03 (m, 4H), 5.51 (d, J=3.7 Hz, 2H), 5.21 (s, 2H), 4.98–4.70 (m, 1H), 4.56 (t, J=9.2 Hz, 1H), 4.40–4.17 (m, 1H), 3.85 (s, 1H), 3.24–3.18 (m, 2H); $^{13}$C NMR (67.5 MHz, CDCl$_3$) δ 157.6, 157.5, 148.4, 139.3, 138.9, 137.0, 136.3, 136.1, 128.9, 128.8, 128.6, 128.4, 128.0, 127.9, 127.6, 123.0, 122.8, 122.3, 121.1, 120.1, 119.8, 118.5, 103.5, 96.6, 83.5, 82.4, 79.6, 77.6, 74.2, 72.4, 71.6, 60.5, 49.9, 49.6, 47.7, 20.9, 14.1; MS (ESI) m/z 533.7 [(M+H)$^+$]; Anal. Calcd for $C_{27}H_{27}F_3N_2O_6$ (532.5): C, 60.90; H, 5.11; N, 5.26; Found: C, 60.68; H, 5.06; N, 5.10.

The compounds of Formulas I, II, and III are useful for the treatment of rheumatoid arthritis, immunomodulatory diseases and disorders, inflammation, and diseases and disorders characterized by exhibiting tissue proliferation.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, method, process step or steps, to the objective, spirit and scope of the present invention. All such modifications are intended to be within the scope of the claims appended hereto.

It should be appreciated that in all invention embodiments described above or in the claims below, whenever an R group such as, for example, R$^1$, R$^2$, R$^3$, R$^4$, R$^5$, or R$^6$, or an n group is used more than once to define an invention compound, each use of the R group and n group is independent of any other use of that same R group or n group or, for that matter, any other R group or n group, unless otherwise specified.

What is claimed is:

1. A compound of Formula (7')

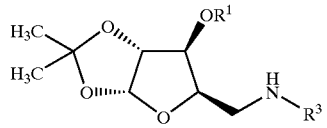

where

R$^1$ is selected from the group consisting of —C$_{1-14}$alkyl and —(CH$_2$)$_{0-4}$-aryl; and R$^3$ is selected from the group consisting of —C$_{1-14}$alkyl, —(CH$_2$)$_{0-2}$-cycloalkyl, —C$_{2-6}$alkenyl, —(CH$_2$)$_{1-4}$-aryl, —(CH$_2$)$_{0-4}$heterocycloalkyl, —(CH$_2$)$_{1-4}$-heteroaryl, and —(CH$_2$)$_{0-2}$—O-aryl:

wherein the compounds of Formula (7') containing:

R$^1$ is benzyl and R$^3$ is isopropyl;

R$^1$ is methyl and R$^3$ is methyl;

R$^1$ is methyl and R$^3$ is ethyl;

R$^1$ is benzyl and R$^3$ is CCH$_2$CO$_2$CH$_2$CH$_3$; and,

R$^1$ benzyl and R$^3$ is CH$_2$CH$_2$OH; are excluded.

* * * * *

UNITED STATES PATENT AND TRADEMARK OFFICE
CERTIFICATE OF CORRECTION

PATENT NO. : 6,794,497 B2  
APPLICATION NO. : 10/054019  
DATED : September 21, 2004  
INVENTOR(S) : Boldi et al.

It is certified that error appears in the above-identified patent and that said Letters Patent is hereby corrected as shown below:

Title Page (75), delete the following inventor names and locations:  
Armen M. Boldi, Burlingame, CA (US);  
Elaine B. Krueger, Pacifica, CA (US);  
Thutam P. Hopkins, Millbrae, CA (US);  
Meghan T. Keaney, Worcester, MA (US)

Signed and Sealed this

Twenty-first Day of August, 2007

JON W. DUDAS  
*Director of the United States Patent and Trademark Office*